(12) United States Patent
Ida et al.

(10) Patent No.: US 11,348,226 B2
(45) Date of Patent: May 31, 2022

(54) MEDICAL IMAGE DIAGNOSTIC APPARATUS

(71) Applicant: Canon Medical Systems Corporation, Otawara (JP)

(72) Inventors: Takashi Ida, Kawasaki (JP); Kenzo Isogawa, Yokohama (JP)

(73) Assignee: Canon Medical Systems Corporation, Otawara (JP)

( * ) Notice: Subject to any disclaimer, the term of this patent is extended or adjusted under 35 U.S.C. 154(b) by 23 days.

(21) Appl. No.: 16/431,240

(22) Filed: Jun. 4, 2019

(65) Prior Publication Data

US 2019/0378270 A1  Dec. 12, 2019

(30) Foreign Application Priority Data

Jun. 7, 2018  (JP) .............................. JP2018-109558

(51) Int. Cl.
*G06T 7/00* (2017.01)
*A61B 5/055* (2006.01)
*G01R 33/48* (2006.01)

(52) U.S. Cl.
CPC ............ *G06T 7/0012* (2013.01); *A61B 5/055* (2013.01); *G01R 33/4818* (2013.01); *G06T 2207/10088* (2013.01); *G06T 2207/20084* (2013.01)

(58) Field of Classification Search
CPC ......... G06T 7/0012; G06T 2207/20084; G06T 2207/10088; G06T 2207/20182;
(Continued)

(56) References Cited

U.S. PATENT DOCUMENTS

2008/0134094 A1\* 6/2008 Samadani ............. G06T 3/0012
715/838
2010/0322375 A1\* 12/2010 Hirokawa ............. A61B 6/032
378/4
(Continued)

FOREIGN PATENT DOCUMENTS

JP          5978429 B2 \*  8/2016  ........... G06T 11/006
JP     2017136170 A  \*  8/2017
(Continued)

OTHER PUBLICATIONS

Kal Zhang, et al., "Beyond a Gaussian Denoiser: Residual Learning of Deep CNN for Image Denoising", IEEE Transactions on Image Processing, vol. 26, Issue. 7, Jul. 2017, 14 pages.
(Continued)

*Primary Examiner* — Matthew C Bella
*Assistant Examiner* — Kathleen M Broughton
(74) *Attorney, Agent, or Firm* — Oblon, McClelland, Maier & Neustadt, L.L.P.

(57) ABSTRACT

According to one embodiment, a medical image diagnostic apparatus includes processing circuitry. The processing circuitry inputs a noise correlation map and a medical image or an intermediate image to a learned model that is functioned to generate a denoise image, in which noise of the medical image or noise of the intermediate image is reduced, based on the medical image generated based on data collected with respect to a subject or the intermediate image at a front stage for generating the medical image and the noise correlation map correlated with the noise included in the medical image or the intermediate image, and generates the denoise image, in which the noise of the medical image or the noise of the intermediate image is reduced.

7 Claims, 15 Drawing Sheets

(58) Field of Classification Search
CPC ... G06T 2207/1008; G06T 2207/20081; G06T 5/002; G06T 5/003; G06T 5/005; G06T 5/006; G06T 11/008; A61B 5/055; G01R 33/4818; G01R 33/565; G01R 33/5608; G01R 33/5611; G06K 9/40; H04N 5/217; G06N 3/08; G06N 3/0454
See application file for complete search history.

(56) References Cited

U.S. PATENT DOCUMENTS

| | | | |
|---|---|---|---|
| 2016/0171727 A1* | 6/2016 | Bouchard | G06K 9/6273 382/131 |
| 2016/0358314 A1* | 12/2016 | Ji | H04N 19/167 |
| 2017/0007148 A1* | 1/2017 | Kaditz | A61B 5/055 |
| 2017/0032222 A1* | 2/2017 | Sharma | G06K 9/4619 |
| 2017/0061620 A1 | 3/2017 | Park et al. | |
| 2018/0144465 A1* | 5/2018 | Hsieh | G06N 3/08 |
| 2018/0349759 A1 | 12/2018 | Isogawa et al. | |

FOREIGN PATENT DOCUMENTS

| | | | | |
|---|---|---|---|---|
| JP | 2018-206382 A | 12/2018 | | |
| KR | 101659578 B1 * | 9/2016 | | G06T 5/001 |
| WO | WO-2016132154 A1 * | 8/2016 | | H04N 19/172 |
| WO | WO-2017223560 A1 * | 12/2017 | | A61B 5/055 |

OTHER PUBLICATIONS

Kenzo Isogawa, et al., "Deep Shrinkage Convolutional Neural Network for Adaptive Noise Reduction", IEEE Signal Processing Letters, vol. 25, No. 2, Feb. 2018, 5 pages.

Japanese Office Action dated Apr. 12, 2022, issued in Japanese Patent Application No. 2018-109558.

* cited by examiner

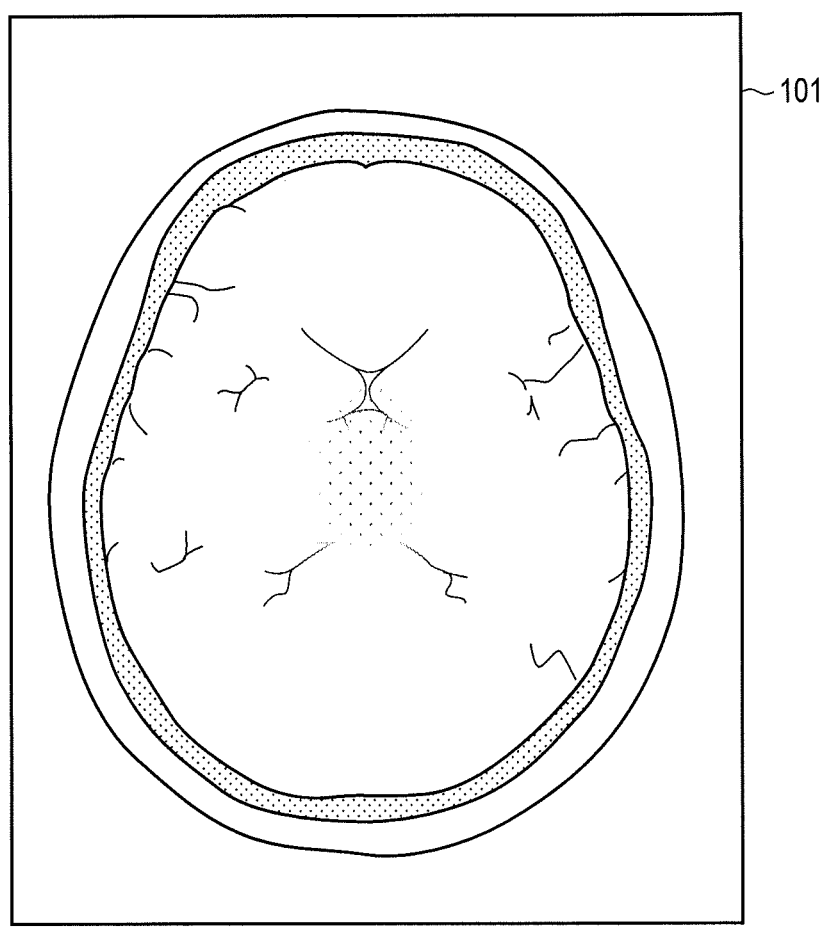
F I G. 13

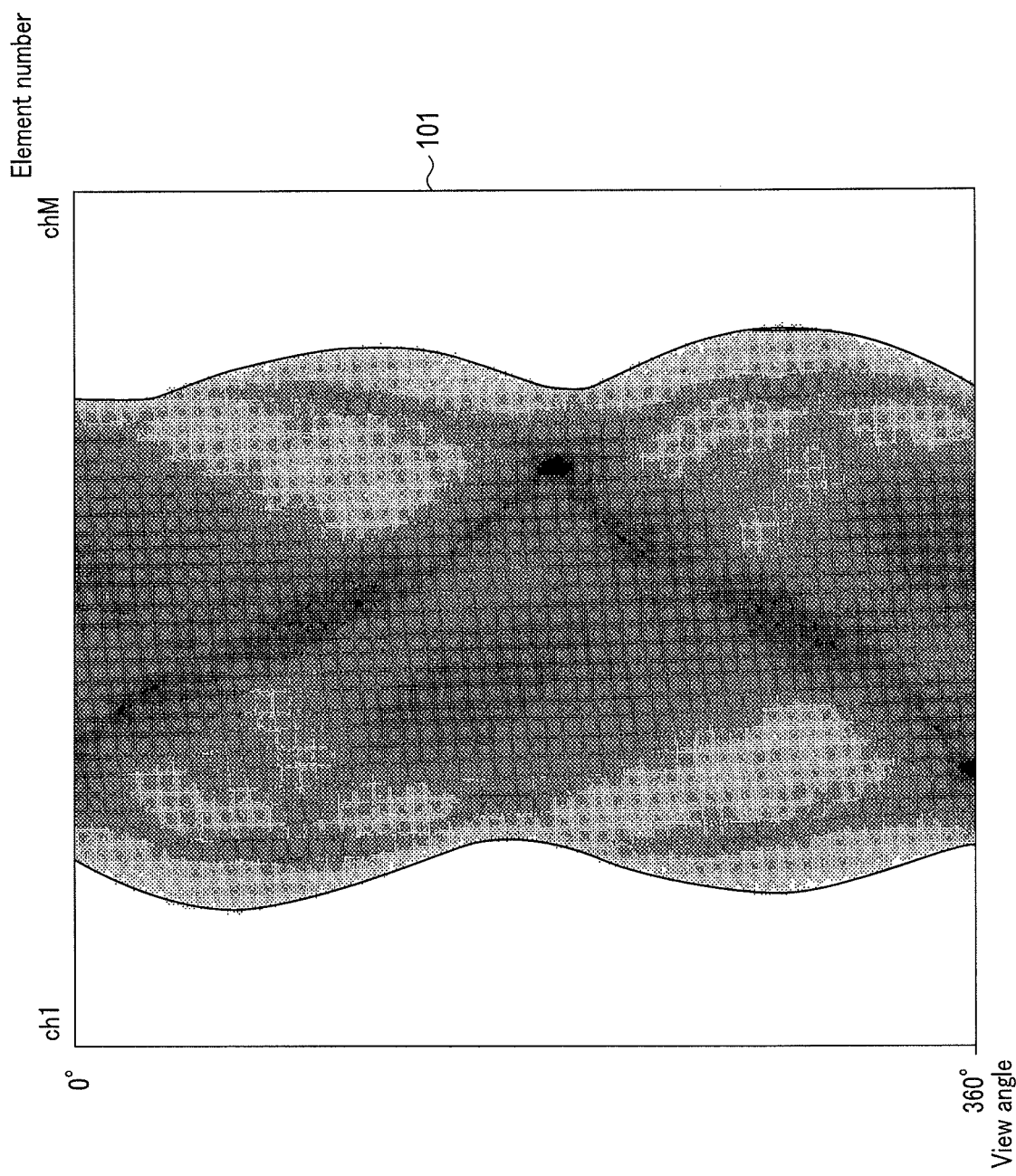
F I G. 16

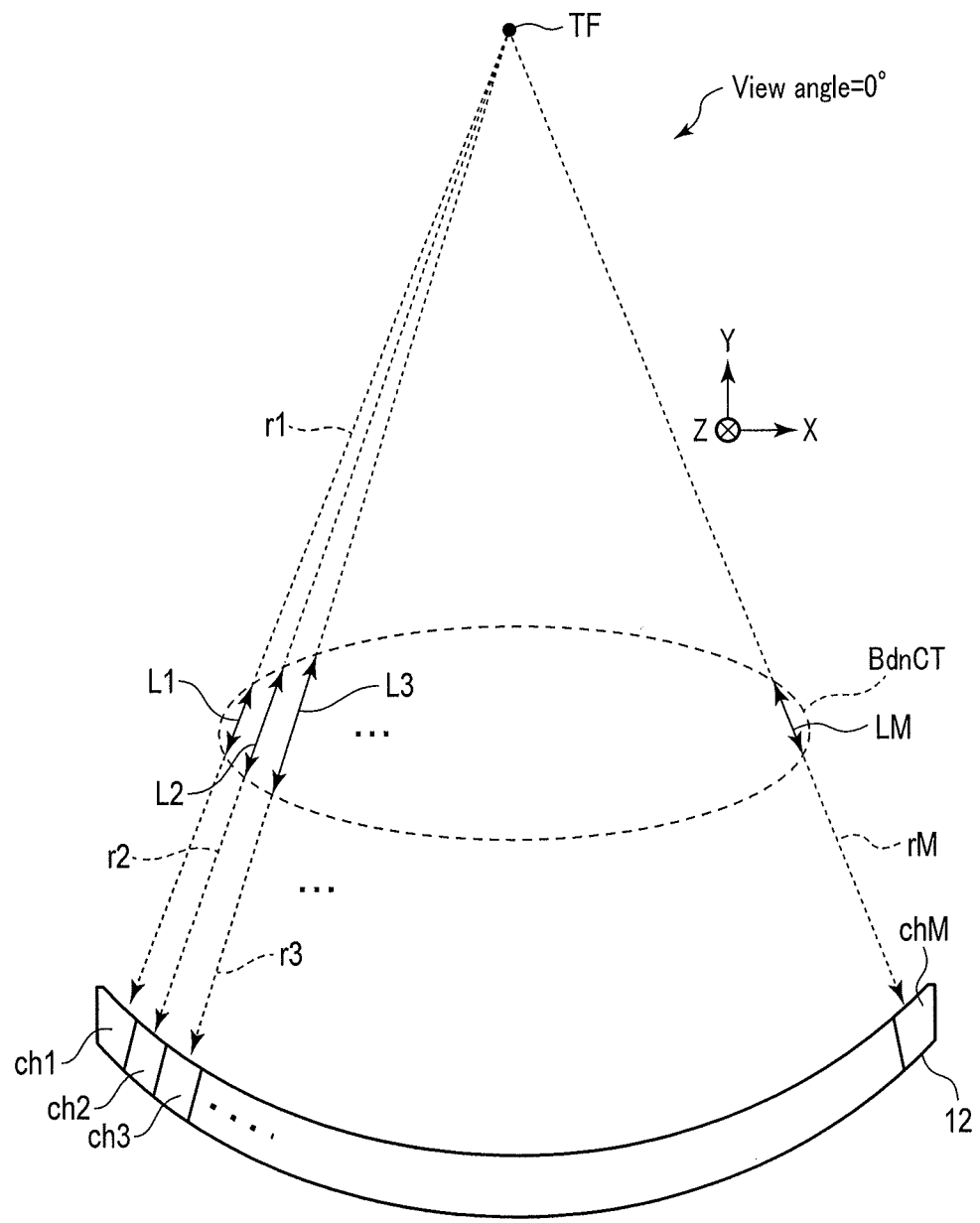
F I G. 17

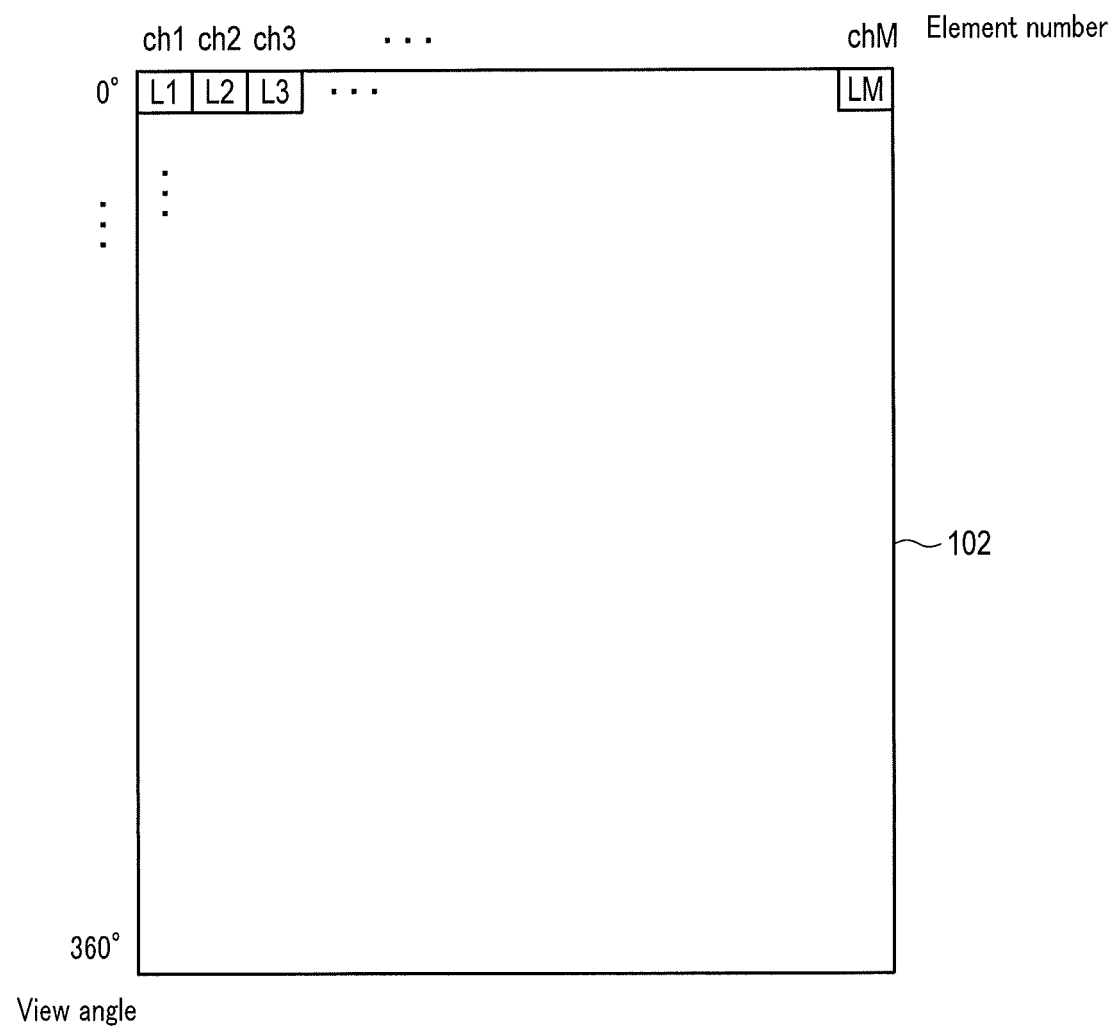
F I G. 18

MEDICAL IMAGE DIAGNOSTIC APPARATUS

CROSS-REFERENCE TO RELATED APPLICATIONS

This application is based upon and claims the benefit of priority from the prior Japanese Patent Application No. 2018-109558, filed Jun. 7, 2018, the entire contents of which are incorporated herein by reference.

FIELD

Embodiments described herein relate to a medical image diagnostic apparatus.

BACKGROUND

Noise included in images acquired by capturing photographs or videos causes various adverse effects such as deterioration in appearance when printed or displayed on a display, deterioration in visibility in security cameras or medical diagnostic apparatuses, and reduction in recognition rate in various image recognition apparatuses. Therefore, it is preferable to remove noise before image display or the like.

Noise removal by image processing is basically realized by suppressing the amplitude of noise through smoothing. At this time, for example, a complicated technique applied to an image pattern may be performed so that an original edge of an image signal (portion where luminance sharply changes) or a texture (fine pattern) is not blurred together with noise. On the other hand, in recent years, an image noise removal method using a simple convolution neural network (hereinafter referred to as CNN) has been proposed as having high signal restoration accuracy.

However, in the image noise removal method using the CNN, since smoothing strength cannot be controlled, the same process is performed on the entire screen. Therefore, for example, noise remains in regions with much noise such as dark portions of the photograph, and an original signal may be smoothed in regions with less noise such as bright portions of the photograph. That is, in the CNN, since convolution is performed using the same weighting factor over the entire region of the input image, noise remains in the region having more noise than noise assumed at the time of learning in the image output from the CNN, and an original pixel value is also smoothed in a region having less noise than noise assumed at the time of learning. However, when the CNN is taught using a wide range of noise amount, there is a problem that the accuracy of noise reduction in images will deteriorate.

BRIEF DESCRIPTIONS OF THE DRAWINGS

FIG. 13 is a diagram illustrating an example of a pre-denoise image generated by the reconstruction function in the first application example of the present embodiment.

FIG. 16 is a diagram illustrating an example of a pre-denoise sinogram in the second application example of the present embodiment.

FIG. 17 is a diagram illustrating an example of a plurality of transmission lengths corresponding to a plurality of element numbers at a view angle of 0° in the second application example of the present embodiment.

FIG. 18 is a diagram illustrating an example of a transmission length map in the second application example of the present embodiment.

DETAILED DESCRIPTION

Figure 1:
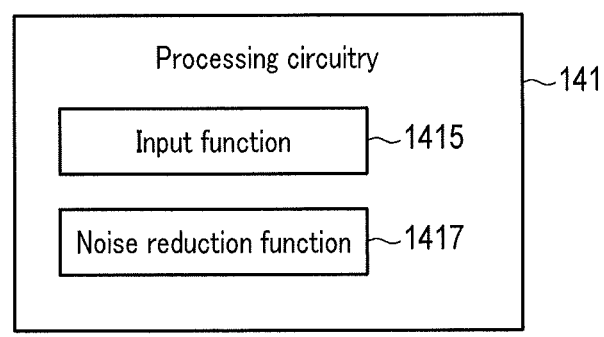
FIG. 1 is a block diagram illustrating a configuration example of processing circuitry mounted on a medical image diagnostic apparatus according to a present embodiment.

According to one embodiment, a medical image diagnostic apparatus includes processing circuitry.

The processing circuitry inputs a noise correlation map and a medical image or an intermediate image to a learned model that is functioned to generate a denoise image, in which noise of the medical image or noise of the intermediate image is reduced, based on the medical image generated based on data collected with respect to a subject or the intermediate image at a front stage for generating the medical image and the noise correlation map correlated with the noise included in the medical image or the intermediate image, and generates the denoise image, in which the noise of the medical image or the noise of the intermediate image is reduced.

An object is to provide a medical image diagnostic apparatus, which is capable of improving the accuracy of noise reduction.

Hereinafter, the present embodiment will be described with reference to the drawings. In the following description, elements having substantially the same configuration are denoted by the same reference numerals, and redundant descriptions thereof are given only when necessary.

FIG. 1 is a block diagram illustrating a configuration example of processing circuitry 141 mounted on a medical image diagnostic apparatus according to a present embodiment. The medical image diagnostic apparatus is, for example, a medical magnetic resonance imaging (hereinafter referred to as MRI) apparatus and a medical x-ray computed tomography (hereinafter referred to as CT) apparatus. A case where the present embodiment is realized by these medical apparatuses will be described later as an application example.

The processing circuitry 141 includes a processor (not illustrated) and a memory such as read only memory (ROM) or random access memory (RAM) as hardware resources. The processing circuitry 141 has an input function 1415 and a noise reduction function 1417. Various functions performed by the input function 1415 and the noise reduction function 1417 are stored in various storage circuitry such as a storage apparatus (not illustrated) or a memory in the form of programs that are executable by a computer. The processing circuitry 141 is a processor that realizes functions corresponding to the respective programs by reading programs corresponding to these various functions from the storage circuitry and executing the read programs. In other words, the processing circuitry 141 in a state in which each program is read has the respective functions illustrated in the processing circuitry 141 of FIG. 1. The input function 1415 and the noise reduction function 1417 of the processing circuitry 141 are examples of an input unit and a noise reduction unit, respectively.

The term "processor" used in the above description may refer to, for example, a circuit such as a central processing unit (CPU), a micro processing unit (MPU), a graphic processing unit (GPU), an application specific integrated circuit (ASIC), a programmable logic device (for example, a simple programmable logic device (SPLD), a complex programmable logic device (CPLD), or a field programmable gate array (FPGA).

The processor realizes the function by reading the program stored in the memory circuitry and executing the read program. Instead of storing the program in the memory circuitry, the program may be directly embedded in the circuit of the processor. In this case, the processor realizes the function by reading the program embedded in the circuit and executing the read program.

Hereinafter, the input function 1415 and the noise reduction function 1417 executed in the processing circuitry 141 will be described with reference to FIGS. 2 to 5.

Figure 2:
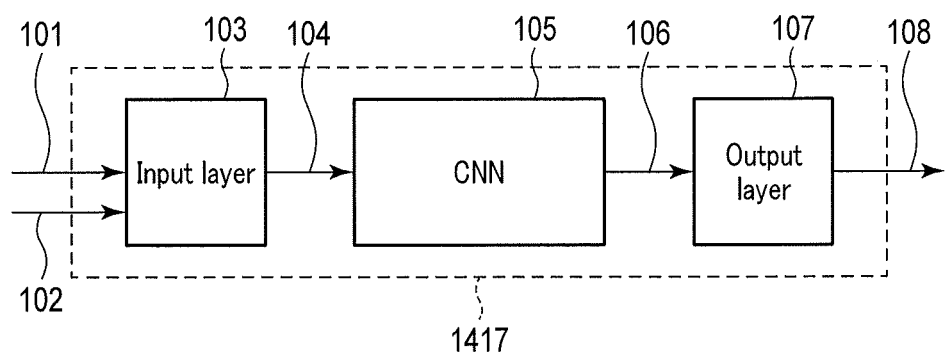
FIG. 2 is a diagram illustrating an example of an outline of a learned model performed in a noise reduction function in the present embodiment.

FIG. 2 is a diagram illustrating an example of an outline of a learned model 105 performed in the noise reduction function 1417. The learned model 105 is a learned machine learning model of a forward propagation network learned from many learning data. The learned model 105 is, for example, a deep neural network (hereinafter referred to as DNN). In the following, for the sake of concrete explanation, explanation will be given taking as an example a convolution neural network (hereinafter referred to as CNN) as a DNN. The learned model 105 is stored in various storage circuitry such as a storage apparatus (not illustrated) and a memory. The learned model 105 is not limited to the DNN and the CNN, and may be other machine learning models. The CNN 105 illustrated in FIG. 2 may include an input layer 103 and an output layer 107. The CNN 105 has a plurality of intermediate layers. Hereinafter, for simplicity of explanation, the CNN 105 will be described as having three intermediate layers. The number of intermediate layers in the CNN 105 is not limited to three, and can be arbitrarily set before CNN learning.

As illustrated in FIG. 2, the process performed in the noise reduction function 1417 includes a process in the input layer 103, a process in the CNN 105, and a process in the output layer 107. In the input layer 103, the input function 1415 sets a processing target signal 101 such as a noise reduction target image and a reference signal 102 such as a noise correlation map correlated with a spatial distribution of noise amount in the processing target signal 101. Hereinafter, for the sake of concrete explanation, noise reduction of an image will be described as an example. At this time, the processing target signal 101 corresponds to the noise reduction target image, and the reference signal 102 corresponds to the image showing the noise correlation map.

When the amount of noise in the noise reduction target image 101 is known, each of a plurality of pixel values in the noise correlation map corresponds to local dispersion or standard deviation of noise. In addition, when contrast correction of different characteristics is performed for each partial region of the image with respect to the noise reduction target image 101, each of the pixel values in the noise correlation map 102 corresponds to a correction value in the contrast correction.

The input layer 103 outputs, to the CNN 105, data (hereinafter referred to as combination data) 104 obtained by combining the noise reduction target image 101 and the noise correlation map 102. The CNN 105 recursively repeats the conversion of the combination data 104, that is, performs the forward propagation process by using the combination data 104 as the input and outputs the converted signal 106 to the output layer 107. Using the converted signal 106, the output layer 107 outputs a signal (hereinafter referred to as a denoise image) 108 in which the noise of the noise reduction target image 101 is reduced.

Figure 3:
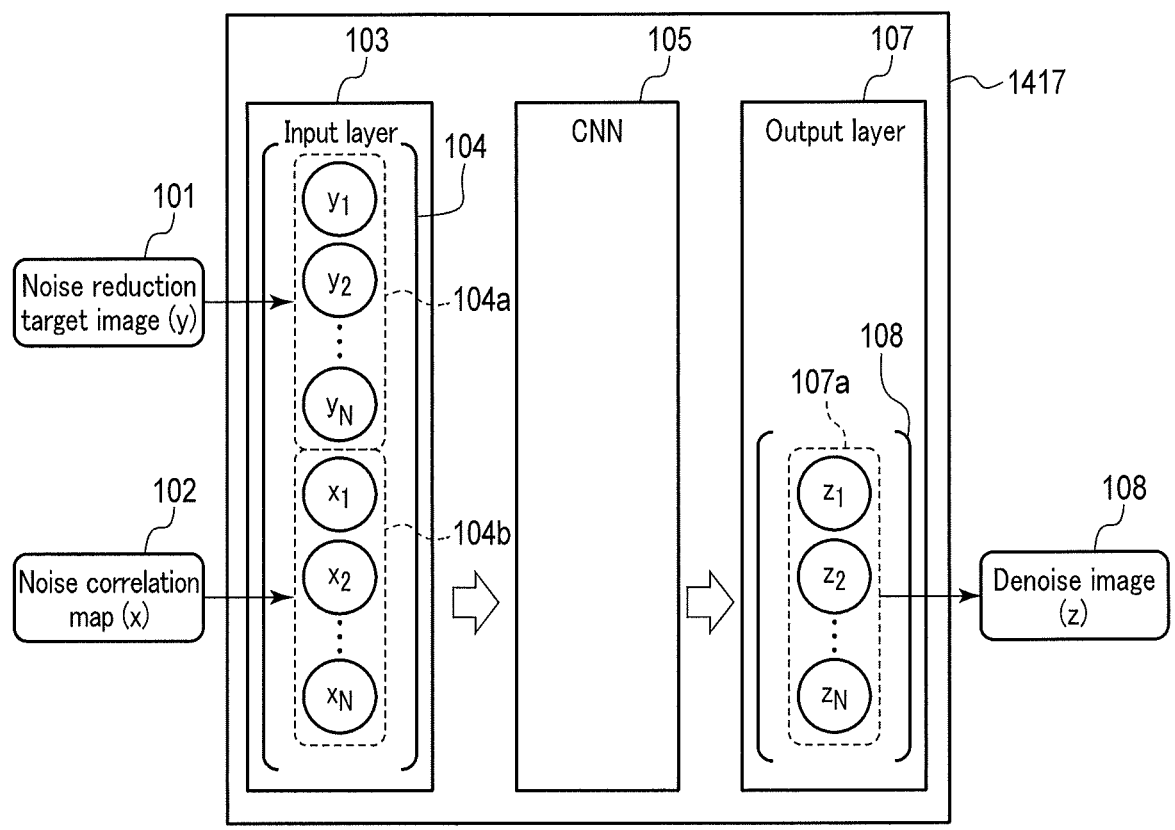
FIG. 3 is a diagram illustrating an example of combination data in an input layer and an output vector generated in an output layer in the present embodiment.

Specifically, the processing circuitry 141 inputs the noise reduction target image 101 and the noise correlation map 102 to the input layer 103 by the input function 1415. That is, the processing circuitry 141 inputs the noise reduction target image 101 and the noise correlation map 102 to different channels of the input layer 103. FIG. 3 is a diagram illustrating an example of the combination data 104 in the input layer 103 and an output vector 107a generated in the output layer 107. In FIG. 3, the combination data 104 is shown as an input vector. The combination data 104 is not limited to the vector format, and may be, for example, a matrix format. For the sake of simplified explanation, it is assumed that the total number of pixels in the noise reduction target image 101 and the noise correlation map 102 is N (N is a natural number).

The processing circuitry 141 generates the combination data 104 by combining a plurality of pixel values in the noise reduction target image 101 and a plurality of pixel values in the noise correlation map 102 in the input layer 103 by the noise reduction function 1417. Specifically, the processing circuitry 141 allocates a plurality of pixel values $(y_1, y_2, \ldots, y_N)$ in the noise reduction target image to a first input range 104a in the input vector 104. In addition, the processing circuitry 141 allocates a plurality of pixel values $(x_1, x_2, \ldots, x_N)$ in the noise correlation map 102 to a second input range 104b in the input vector 104. The processing circuitry 141 outputs the input vector 104 to the CNN 105. When outputting from the input layer 103 to the CNN 105, the processing circuitry 141 performs a convolution process on the input vector 104. The processing circuitry 141 recursively performs a convolution process in the CNN 105. The convolution process and the like will be described in detail later with reference to FIG. 4. When the number of pixels in the noise reduction target image 101 is different from the number of pixels in the noise correlation map, the processing circuitry 141 appropriately adjusts the number of pixels in the noise correlation map 102 to the number of pixels in the noise reduction target image by an existing method.

The processing circuitry 141 holds the signal 106 output from the CNN 105 by the noise reduction function 1417 as the vector format 107a indicating pixel values $(z_1, z_2, \ldots, z_N)$ of the denoise image 108 in the output layer 107. The processing circuitry 141 generates the denoise image 108 by rearranging a plurality of components in the vector format 107a as the pixels. The processing circuitry 141 outputs the denoise image 108 to the storage apparatus or the like.

Figure 4:
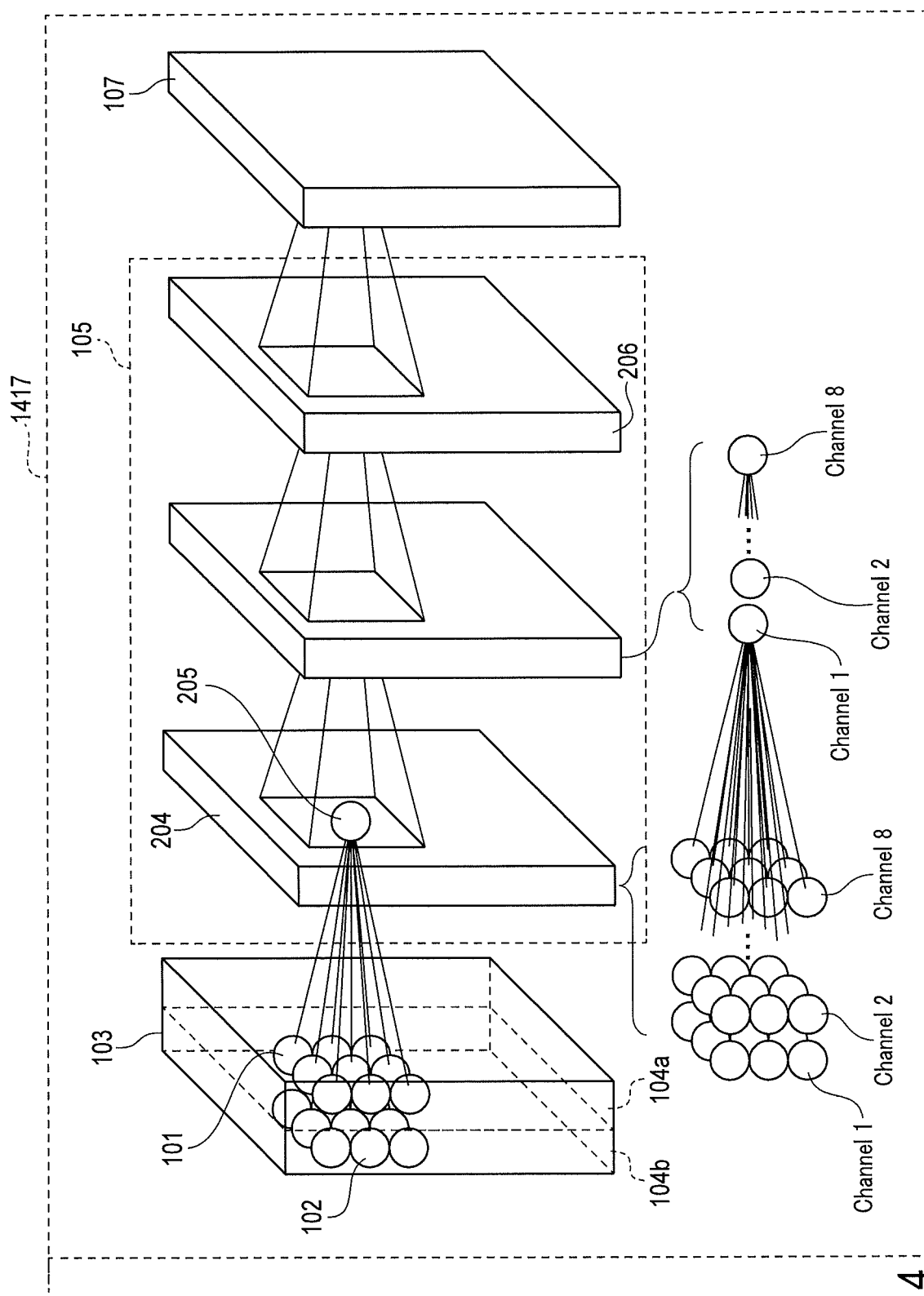
FIG. 4 is a diagram illustrating an example of a configuration of a convolution neural network (CNN) in the present embodiment.

FIG. 4 is a diagram illustrating an example of the configuration of the CNN 105. In FIG. 4, the input layer 103, the CNN 105, a first intermediate layer 204, and the output layer 107 are illustrated as perspective views for convenience of explanation. First, the processing circuitry 141 sets the pixel values of the noise reduction target image to a plurality of nodes included in the first input range 104a in the input layer 103 by the noise reduction function 1417. In addition, the processing circuitry 141 sets the pixel values of the noise correlation map 102, to a plurality of nodes included in the second input range 104b in the input layer 103. In FIG. 4, a plurality of nodes other than circles indicating nine nodes in each of the first input range 104a and the second input range 104b are omitted for clarity. The nodes in the first input range 104a and the second input range 104b are prepared by the number of pixels of the noise reduction target image.

Next, the processing circuitry 141 performs a convolution process on the noise reduction target image 101 and the noise correlation map 102 by using a filter having a plurality of learned weighting coefficients by the noise reduction function 1417. The processing circuitry 141 generates data to be input from the input layer 103 to the first intermediate layer 204 by the convolution process. The total number of weighting coefficients (hereinafter referred to as taps) in the filter is smaller than the number of pixels to which the filter is applied. For example, in the input layer 103 of FIG. 4, the tap is 18 since the number of pixels to which the filter is applied is 3 pixels (horizontal)×3 pixels (vertical)×2 images (noise reduction target image 101 and noise correlation map 102). The tap is not limited to 18 as illustrated in FIG. 4, and may be set as appropriate at the time of learning.

The processing circuitry 141 performs a product-sum operation for nine pixels in the noise reduction target image 101 and nine pixels in the noise correlation map 102 by using the filter whose taps have 18 weighting coefficients by the noise reduction function 1417. In the first intermediate layer 204, the processing circuitry 141 sets the result value (hereinafter referred to as a product-sum value) of the product-sum operation to the node 205 corresponding to the position of the filter used for the product-sum calculation. The processing circuitry 141 sets the product-sum value for all the nodes in the first intermediate layer 204 while changing the application position of the filter to the noise reduction target image 101 and the noise correlation map 102. The number of all the nodes in the first intermediate layer 204 is the same as the total number of pixels in the noise reduction target image 101 and the noise correlation map 102. The number of all the nodes may also be different from the total number of pixels, in the noise reduction target image 101 and the noise correlation map 102. In addition, the values of the weighting coefficients included in the filter are constant regardless of the positions of the filters applied to the noise reduction target image 101 and the noise correlation map 102.

Figure 5:
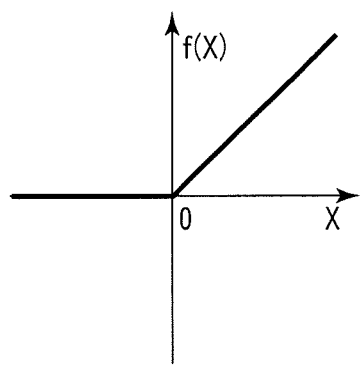
FIG. 5 is a diagram illustrating an example of an activation function according to the present embodiment.

The processing circuitry 141 converts (activates) the output result from the filter, that is, a product-sum value X, by using a nonlinear function called an activation function by the noise reduction function 1417. FIG. 5 is a diagram illustrating an example of an activation function f(X). The processing circuitry 141 uses a rectified linear unit (ReLU) function shown in FIG. 5 as the activation function. The activation function f(X) shown in FIG. 5 is a function that outputs 0 when X≥0 and outputs X when X>0. The activation function is not limited to the ReLU function, and can be set appropriately at the time of learning by the CNN 105. Each of the intermediate layers in the CNN 105 may have a plurality of channels corresponding to the number of images. For example, as illustrated in FIG. 4, when the number of channels in the first intermediate layer 204 is 8, the processing circuitry 141 uses eight filters of 3×3×2 taps for each channel in the conversion from the input layer 103 to the first intermediate layer 204. For the eight types of the filters, the weighting coefficients are different. The taps of the filters used in each of the intermediate layers may be different.

Similarly, when the number of channels from the i-th intermediate layer (i is a natural number from 1 to (n−1) and n is the total number of the intermediate layers) to the (i+1)th intermediate layer is 8, the processing circuitry 141 repeats image conversion (n−1) times by using eight filters of 3×3×8 taps and the activation function by the noise reduction function 1417. For example, as illustrated in FIG. 4, when the total number of intermediate layers is 3, the processing circuitry 141 performs the conversion of the product-sum value from the intermediate layer to the intermediate layer twice.

The number of channels of the output layer 107 is set to 1 at the time of learning. For example, in the case illustrated in FIG. 4, the processing circuitry 141 performs the product-sum operation by using one filter of the 3×3×8 taps for the product-sum value of eight channels of the third intermediate layer 206 in the output layer 107 by the noise reduction function 1417. The processing circuitry 141 sets the result (product-sum value) obtained by the product-sum operation to the channels of the output layer 107 as the pixel value without using the activation function. The processing circuitry 141 generates the denoise image by using the pixel value set in the output layer 107.

Note that the weighting coefficients in each of the filters used in the CNN 105 are learned by a method called an error back propagation method by using many learning data before implementing the noise reduction function 1417. Specifically, the weighting coefficients are learned so that the output image obtained when the image containing noise (hereinafter referred to as a noise-containing image) and the noise correlation map are input is closer to the denoise image. Each of many learning data is generated by, for example, the following procedure. First, the image without noise (hereinafter referred to as a non-noise image) and the noise correlation map 102 are prepared. Next, Gaussian noise having the pixel value of the noise correlation map 102 as the standard deviation is added to a plurality of pixel values in the non-noise image to generate a noise-containing image. The non-noise image, the noise correlation map 102, and the noise-containing image are generated as a set of learning data.

In addition to the configuration of FIG. 4, the processing circuitry 141 in the present embodiment may perform a process called batch normalization after convolution in the intermediate layer. In addition, the processing circuitry 141 may generate the denoise image by outputting the noise image, instead of outputting the denoise image, by the noise reduction function 1417, and then subtracting the noise image from the noise reduction target image 101. At this time, the weighting coefficients are learned so that the output image at the time of inputting the noise-containing image and the noise correlation map approaches an image showing noise (hereinafter referred to as a noise image). The noise image corresponds to an image showing Gaussian noise with the pixel value of the noise correlation map as the standard deviation.

According to the processes by the above-described configuration, the following effects can be obtained.

According to the processing circuitry 141 of the present embodiment, since the reference signal 102 is also input to the input layer 103 in addition to the processing target signal 101, the degree of freedom in which the output changes according to the amount of noise is generated even with the same weighting factor from the input layer 103 toward the first intermediate layer 204 in the learning of the CNN 105. Therefore, according to the present embodiment, as compared with the case where only the noise reduction target image is input to the input layer 103, even when the amount of noise in the noise reduction target image 101 is different in each of the regions of the image, it is possible to reduce noise in the processing target signal 101 with an intensity corresponding to the amount of noise for each partial region in the processing target signal 101.

(First Modification Example)

Figure 6:
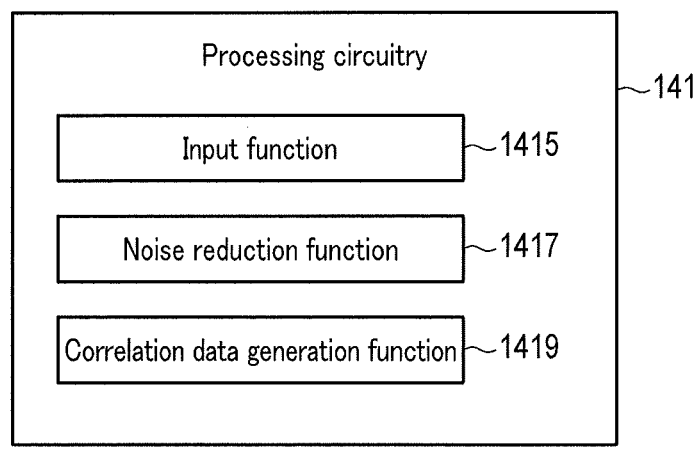
FIG. 6 is a block diagram illustrating a configuration example of processing circuitry in a first modification example of the present embodiment.

A difference between the present modification example and the present embodiment is to generate the noise correlation map 102 based on the noise reduction target image 101 by using a second learned model. FIG. 6 is a block diagram showing a configuration example of the processing circuitry 141 in the present modification example. The processing circuitry 141 illustrated in FIG. 6 further has a correlation data generation function 1419 in addition to the various functions of the processing circuitry 141 illustrated in FIG. 1. The correlation data generation function 1419 of the processing circuitry 141 is an example of a correlation data generation unit.

The processing circuitry 141 performs the second learned model by the correlation data generation function 1419. The second learned model is a learned machine learning model of a forward propagation network learned from many learning data. The second learned model is, for example, a CNN including an input layer, a plurality of intermediate layers, and an output layer. The second learned model is stored in various storage circuitry such as a storage apparatus (not illustrated) and a memory. The second learned model may be a DNN including an input layer, a plurality of intermediate layers, and an output layer. Since the second learned model in the present modification example is the CNN or the DNN, detailed descriptions thereof will be omitted.

The weighting coefficients in each of the filters used in the CNN in the present modification example are learned by a method called an error back propagation method by using many learning data before implementing the correlation data generation function 1419. Each of many learning data is used to learn a plurality of weighting coefficients by using the noise-containing image and the noise correlation map as a set of learning data. That is, the weighting coefficients are learned so that the output image at the time of inputting the noise-containing image approaches the noise correlation map.

Figure 7:
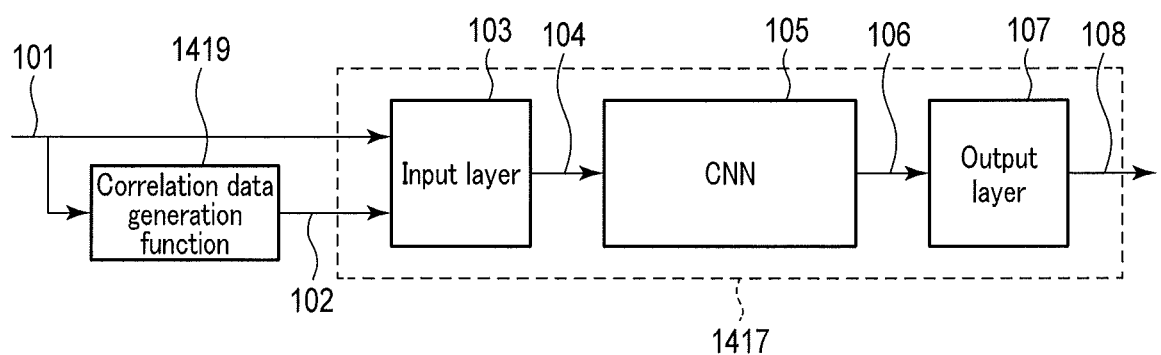
FIG. 7 is a diagram illustrating an example of data input in the first modification example of the present embodiment.

FIG. 7 is a diagram illustrating an example of data input in the present modification example. Hereinafter, a process related to the difference between the present modification example and the present embodiment will be described with reference to FIG. 7.

The processing circuitry 141 inputs the noise reduction target image 101 to the input layer 103 and the input layer 103 of the second learned model in the correlation data generation function 1419 by the input function 1415. In addition, the processing circuitry 141 inputs the noise correlation map 102 output from the correlation data generation function 1419 to the input layer 103.

The processing circuitry 141 generates the noise correlation map 102 by performing the second learned model, to which the noise reduction target image 101 is input, by the correlation data generation function 1419. Since the processing contents of the noise reduction function 1417 are the same as those in the present embodiment, descriptions thereof will be omitted. Note that the processing of the correlation data generation function 1419 may be embedded in the noise reduction function 1417.

According to the configuration described above, the following effects can be obtained in addition to the effects of the present embodiment.

According to the processing circuitry 141 of the present modification example, since the reference signal 102 can be generated from the processing target signal 101, there is no need to prepare the reference signal 102 separately from the processing target image 101. That is, according to the present processing circuitry 141, since it is unnecessary to collect the reference signal 102, it is possible to improve the efficiency related to the denoise process of the processing target image 101.

(Second Modification Example)

A difference between the present modification example and the present embodiment is that only the noise reduction target image 101 is input to the input layer 103 and the noise correlation map 102 is input to at least one intermediate layer in the CNN 105. That is, the input layer 103 in the present modification example has only the first input range 104a. In addition, in the present modification example, the intermediate layer to which the noise correlation map 102 is input has a channel to which the noise correlation map 102 is input in addition to a channel to which the product-sum value activated by the activation function is input.

Figure 8:
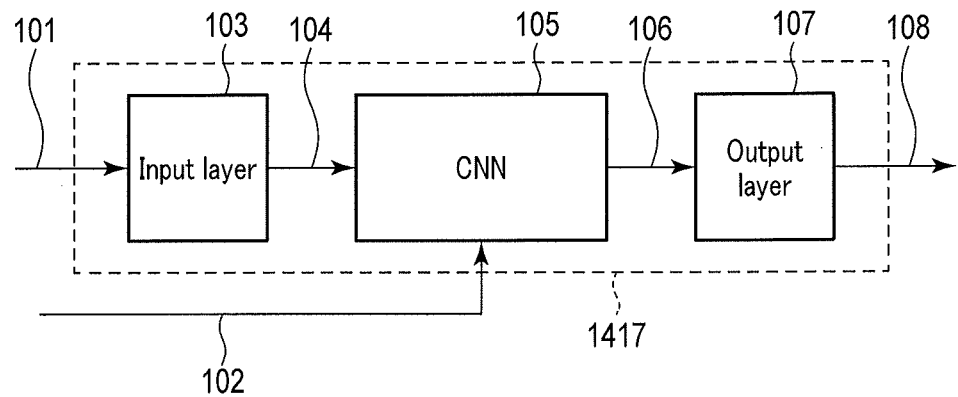
FIG. 8 is a diagram illustrating an example of data input in a second modification example of the present embodiment.

FIG. 8 is a diagram illustrating an example of data input in the present modification example. Hereinafter, a process related to the difference between the present modification example and the present embodiment will be described with reference to FIG. 8. Learning for the CNN 105 in the present modification example is the same as the present embodiment, except that the input to the input layer 103 is only the noise reduction target image 101, and the input of the noise correlation map 102 to the CNN 105 is the intermediate layer, and thus a description thereof will be omitted.

The processing circuitry 141 inputs the noise reduction target image 101 to the input layer 103 by the input function 1415. The processing circuitry 141 inputs the noise correlation map 102 to the intermediate layer of the CNN 105. For the sake of concrete explanation, it is assumed that the intermediate layer to which the noise correlation map 102 is input is the first intermediate layer 204. The intermediate layer to which the noise correlation map 102 is input is not limited to the first intermediate layer 204, and the noise correlation map 102 may be input to any one of the intermediate layers.

Figure 9:
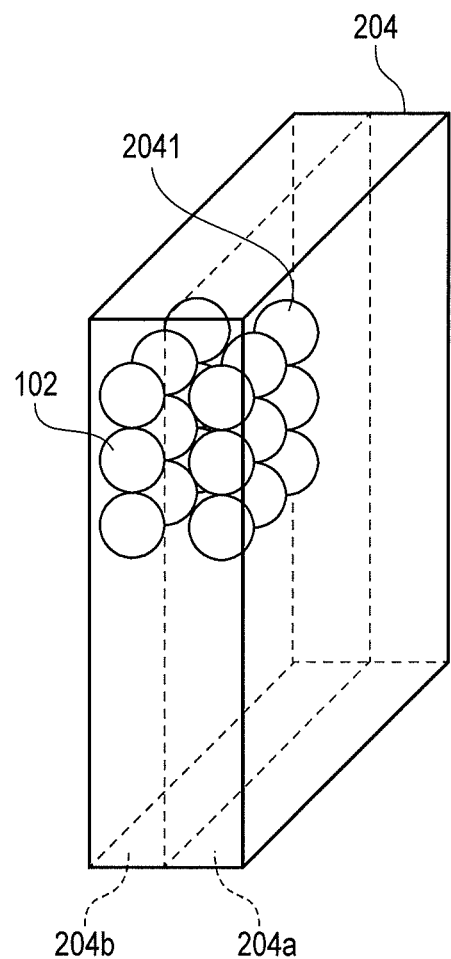
FIG. 9 is a diagram illustrating an example of a first intermediate layer to which a noise correlation map is input in the second modification example of the present embodiment.

FIG. 9 is a diagram illustrating an example of the first intermediate layer 204 to which the noise correlation map 102 is input in the present modification example. As illustrated in FIG. 9, the first intermediate layer 204 includes a post-convolution input range 204a to which the convoluted and activated data 2041 is input from the input layer 103, and a map input range 204b to which the noise correlation map 102 is input. A plurality of nodes in the post-convolution input range 204a are the same as a plurality of nodes in the first input range 104a. In addition, a plurality of nodes in the map input range 204b are the same as a plurality of nodes in the second input range 104b. That is, in the present modification example, the first intermediate layer 204 has a channel to which the noise correlation map 102 is input, in addition to the channel described in the present embodiment. Therefore, the processing circuitry 141 performs convolution with a tap with many taps in the channel direction as many added channels, as the output to the second intermediate layer by the noise reduction function 1417. For example, referring to FIGS. 4 and 9, the processing circuitry 141 performs a convolution process by using a filter of 3×3×9 taps.

The input of the noise correlation map 102 to the intermediate layer may be simply added to the convolution data, without using the channel for the noise correlation map and the map input range 204b in the above example. That is, the value of the noise correlation map corresponding to each node may be added to the value set in the input range 204a. In addition, in a case where there are two or more channels of input range 204a, the noise correlation map may be input to the configuration similar to the input layer 103, and the output increased from one channel may be added to each node and each channel of the input range 204a.

According to the above-described configuration, in the present modification example, similarly to the effect of the present embodiment, since the degree of freedom in which the output is changed according to the amount of noise is obtained in the intermediate layer to which the reference signal 102 is input, it is possible to reduce the noise of the processing target signal 101 with intensity corresponding to the amount of noise for each partial range in the processing target signal 101.

Hereinafter, as a medical image diagnostic apparatus including the processing circuitry 141 in the present embodiment, a first application example and a second application example for the medical MRI apparatus and the medical X-ray CT apparatus will be described. The noise reduction target image 101 and the noise correlation map 102 differ in accordance with the type of modality in the medical image diagnostic apparatus. Therefore, the noise reduction target image 101 and the noise correlation map 102 input to the input layer 103 by the input function 1415 will be described in each of the medical MRI apparatus and the medical X-ray CT apparatus.

(First Application Example)

The medical image diagnostic apparatus in the present application example is a medical MRI apparatus on which the processing circuitry 141 in the present embodiment is mounted. In the present application example, the noise reduction target image 101 corresponds to a medical image. In addition, the noise correlation map 102 is an image correlated with the spatial distribution of noise amount in the medical image.

Specifically, the medical image in the present application example corresponds to an MR image (hereinafter referred to as a pre-denoise image) obtained before the denoise process by the noise reduction function 1417 in FIG. 1, and reconstructed based on magnetic resonance (hereinafter referred to as MR) data collected by a main scan performed on a subject P. In addition, the noise correlation map 102 in the present application example corresponds to a sensitivity map or a g map acquired by a scan (hereinafter referred to as a prescan) executed before the main scan. The noise correlation map 102 is not limited to the sensitivity map or the g map, and may be any image as long as it is an image that correlates with the noise amount in the MR image. Furthermore, the prescan can be executed after the main scan.

For example, a map (hereinafter referred to as a sensitivity-g map) generated by the processing circuitry 141 using the sensitivity map and the g map may also be used as the noise correlation map 102. Here, the sensitivity-g map has characteristics of the sensitivity map and the g map. The sensitivity-g map is, for example, an image obtained by combining the sensitivity map and the g map, an added image of the sensitivity map and the g map, a convolution image, or a superimposed image. Furthermore, as the noise correlation map 102, an image generated by a prescan executed without generating an RF pulse (hereinafter referred to as an RF non-transmission map) may also be used. The RF non-transmission map, for example, correlates with an electric white noise that is caused by a dark current, etc. in a receive coil 127 and reception circuitry 129. Furthermore, as the noise correlation map 102 corresponding to each of a plurality of time-series images generated by executing a main scan over a number of times, a subtraction image generated by subtracting each of the time-series images from an average image calculated by the plurality of time-series images may be used. The subtraction image to be used as the noise correlation map 102 may also be generated by subtracting each of the time-series images from an MR image of a reference time in the plurality of time-series images. The subtraction image to be used as the noise correlation map 102 may also be generated by differentiating the two adjacent MR images in the plurality of time-series images. The subtraction image to be used as the noise correlation map 102 may also be a subtraction image of a median filter-processed image, which is obtained by executing median filter processing with respect to the MR image generated by executing the main scan, and the MR image.

The sensitivity map is an image showing spatial distribution (spatial sensitivity) of the sensitivity of the receive coil used in the main scan. The g map is an image showing a g-factor indicating the extent in which the noise amplifies in unfolding processing regarding parallel imaging for each pixel.

In the present application example, since the processing contents regarding the first modification example and the second modification example can be understood by replacing the noise reduction target image 101 with the MR image, and replacing the noise correlation map 102 with the sensitivity map (or the g map or the sensitivity-g map), descriptions thereof will be omitted.

Figure 10:
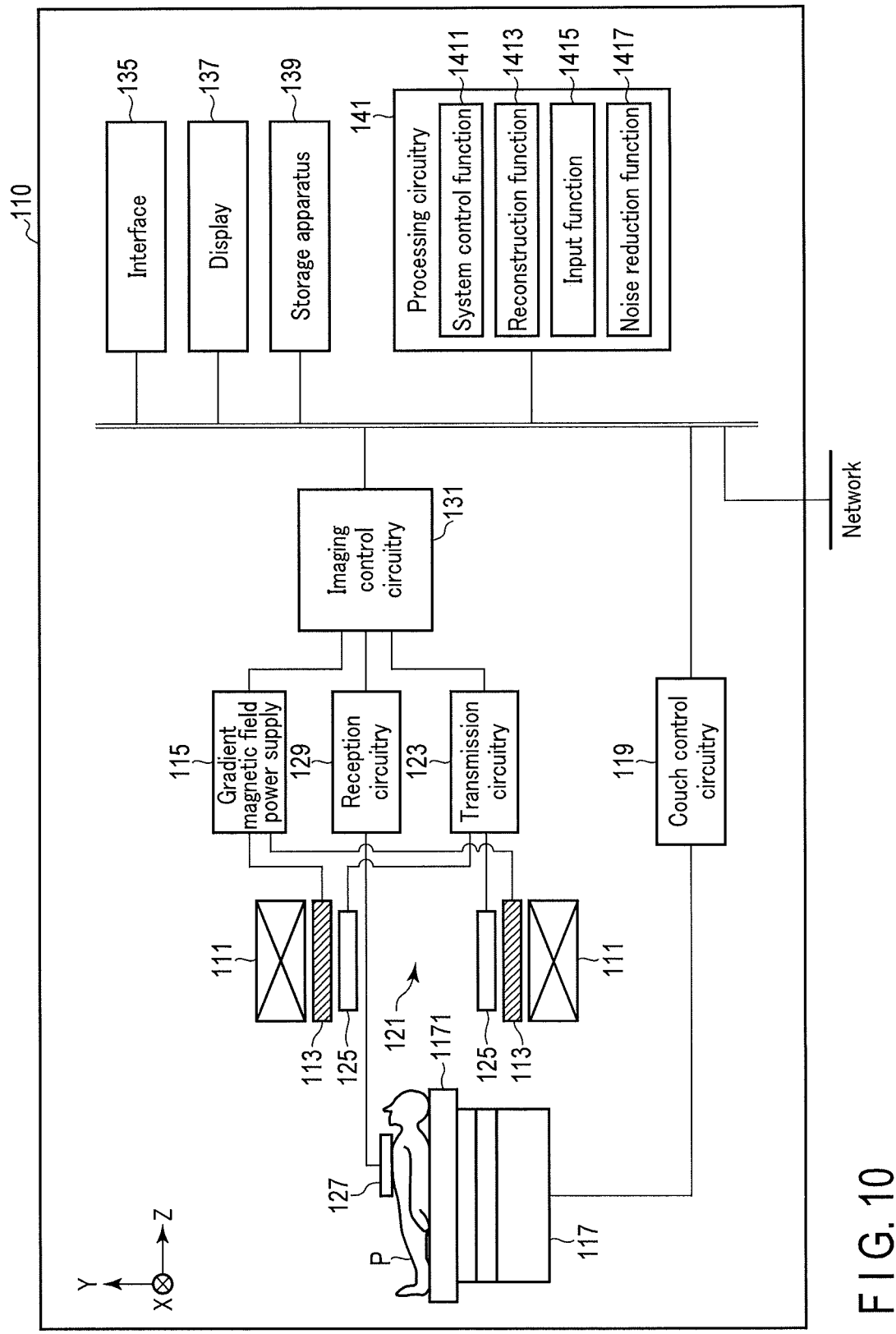
FIG. 10 is a diagram illustrating an example of a configuration of a medical MRI apparatus in a first application example of the present embodiment.

The overall configuration of a medical MRI apparatus 110 in the present embodiment will be described with reference to FIG. 10. FIG. 10 is a diagram illustrating an example of a configuration of the medical MRI apparatus 110. As illustrated in FIG. 10, the medical MRI apparatus 110 includes a static field magnet 111, a gradient coil 113, a gradient magnetic field power supply 115, a couch 117, couch control circuitry 119, transmission circuitry (transmitter) 123, a transmit coil 125, a receive coil 127, reception circuitry (receiver) 129, imaging control circuitry (imaging control unit) 131, an interface (interface unit) 135, a display (display unit) 137, a storage apparatus (memory) 139, and processing circuitry (processor) 141. As illustrated in FIG. 10, the processing circuitry 141 includes a system control function 1411, a reconstruction function 1413, an input function 1415, and a noise reduction function 1417.

In the present application example, in a case where the noise correlation map is generated from the pre-denoise image as described in the first modification example, the processing circuitry 141 in the medical MRI apparatus 110 further includes a correlation data generation function 1419 as illustrated in FIG. 6.

The system control function 1411, the reconstruction function 1413, the input function 1415, the noise reduction function 1417, and the correlation data generation function 1419 included in the processing circuitry 141 are respectively examples of a system control unit, a reconstruction unit, an input unit, a noise reduction unit, and a correlation data generation unit. The process performed by the correlation data generation function 1419 may be performed by the noise reduction function 1417. The subject P is not included in the medical MRI apparatus 110.

The static field magnet 111 is a hollow approximately-cylindrical magnet. The static field magnet 111 generates a uniform static magnetic field ($B_0$) in the inner space. For example, a superconductive magnet or the like is used as the static field magnet 111.

The gradient coil 113 is a hollow cylindrical coil. The gradient coil 113 is provided on the inner side of the static field magnet 111. The gradient coil 113 is a combination of three coils corresponding to each of X, Y, and Z-axes orthogonal to one another. The Z-axis direction is the same direction as the direction of the static magnetic field. The Y-axis direction is a vertical direction, and the X-axis direction is a direction perpendicular to the Z-axis and the Y-axis. The three coils in the gradient coil 113 are individually supplied with a current from the gradient magnetic field power supply 115, and generate gradient magnetic fields whose magnetic field intensity changes along the respective X, Y, and Z-axes.

The gradient magnetic fields of each of the X, Y, and Z-axes generated by the gradient coil 113 form, for example, a slice selection gradient magnetic field, a phase encoding gradient magnetic field, and a frequency encoding gradient magnetic field (also referred to as a readout gradient magnetic field). The slice selection gradient magnetic field is used to determine an imaging slice as appropriate. The phase encoding gradient magnetic field is used to change the phase of an MR signal in accordance with the spatial position. The frequency encoding gradient magnetic field is used to change the frequency of an MR signal in accordance with the spatial position. Furthermore, the gradient magnetic fields of the respective X, Y, and Z-axes generated by the gradient coil 113 are used as a re-convergence pulse in which the direction of the gradient magnetic fields is inverted twice in order to reconverge the phase of a spin on an X-Y plane in a gradient echo method. In addition, the gradient magnetic fields of the respective X, Y, and Z-axes generated by the gradient coil 113 are used as an offset of a first shimming of the static magnetic field.

The gradient magnetic field power supply 115 is a power supply device that supplies a current to the gradient coil 113 under the control of the imaging control circuitry 131.

The couch 117 is an apparatus including a couch top 1171 on which the subject P is placed. The couch 117 inserts the couch top 1171 on which the subject P is placed into a bore 121 under the control of the couch control circuitry 119. The couch 117 is installed in an examination room in such a manner that, for example, its longitudinal direction is parallel to the central axis of the static field magnet 111.

The couch control circuitry 119 is circuitry that controls the couch 117. The couch control circuitry 119 drives the couch 117 in response to an operator's instruction via the interface 135 to move the couch top 1171 in the longitudinal direction and vertical direction, and, in some cases, the horizontal direction.

The transmission circuitry 123 supplies a radio frequency pulse that has been modulated by the Larmor frequency to the transmit coil 125 under the control of the imaging control circuitry 131.

The transmit coil 125 is an RF coil that is provided on the inner side of the gradient coil 113. The transmit coil 125 generates a radio frequency (RF) pulse corresponding to a high-frequency magnetic field in accordance with the output from the transmission circuitry 123. The transmit coil 125 is, for example, a whole body coil (hereinafter referred to as a WB coil) that includes a plurality of coil elements. The WB coil may be used as a transmit/receive coil. Furthermore, the transmit coil 125 may be a WB coil formed by one coil.

The receive coil 127 is an RF coil provided on the inner side of the gradient coil 113. The receive coil 127 receives an MR signal that the high-frequency magnetic field causes the subject P to emit. The receive coil 127 outputs the received MR signal to the reception circuitry 129. The receive coil 127 is, for example, a coil array that has one or more, and typically a plurality of coil elements. FIG. 10 shows the transmit coil 125 and the receive coil 127 as separate RF coils; however, the transmit coil 125 and the receive coil 127 may be embodied as an integrated transmit/receive coil. The transmit/receive coil corresponds to the imaging portion of the subject P, and is a local transmit/receiver RF coil such as a head coil.

The reception circuitry 129 generates a digital MR signal (hereinafter referred to as MR data) based on the MR signal output from the receive coil 127 under the control of the imaging control circuitry 131. Specifically, the reception circuitry 129 performs various types of signal processing on the MR signal output from the receive coil 127, and then performs analog-to-digital (A/D) conversion on the data subjected to the various types of signal processing. The reception circuitry 129 samples the A/D-converted data. The reception circuitry 129 thereby generates the MR data. The reception circuitry 129 outputs the generated MR data to the imaging control circuitry 131.

In accordance with an imaging protocol output from the processing circuitry 141, the imaging control circuitry 131 controls, for example, the gradient magnetic field power supply 115, the transmission circuitry 123, and the reception circuitry 129, and performs imaging on the subject P. The imaging protocol includes various pulse sequences corresponding to the examination. The imaging protocol defines the magnitude of the current supplied from the gradient magnetic field power supply 115 to the gradient coil 113, timing of the supply of the current from the gradient magnetic field power supply 115 to the gradient coil 113, the magnitude and time width of the radio frequency pulse supplied from the transmission circuitry 123 to the transmit coil 125, timing of the supply of the radio frequency pulse from the transmission circuitry 123 to the transmit coil 125, and timing of reception of the MR signal at the receive coil 127, etc.

The imaging control circuitry 131 executes a prescan, and outputs MR data collected by the prescan (hereinafter referred to as prescan-MR data) to the processing circuitry 141. For the imaging method to acquire the prescan-MR data regarding the sensitivity map and the g map, various imaging protocols that are known are used. Furthermore, the imaging control circuitry 131 executes a main scan and outputs MR data collected by the main scan (hereinafter referred to as main scan-MR data) to the processing circuitry 141.

The interface 135 includes a circuit that receives various instructions and information inputs from the operator. The interface 135 includes a circuit relating to, for example, a pointing device such as a mouse, or an input device such as a keyboard. The circuit included in the interface 135 is not limited to a circuit relating to a physical operational component, such as a mouse or a keyboard. For example, the interface 135 may include an electrical signal processing circuit that receives an electrical signal corresponding to an input operation from an external input device provided separately from the present medical MRI apparatus 110 and outputs the received electrical signal to various circuits.

The display 137 displays, for example, a denoise image corresponding to various MR images generated by the noise reduction function 1417, and various types of information on imaging and image processing, under the control of the system control function 1411 in the processing circuitry 141. The display 137 is, for example, a display device, such as a cathode ray tube (CRT) display, a liquid crystal display, an organic EL display, a light-emitting diode (LED) display, a plasma display, or any other display or monitor known in the relevant technical field.

A storage apparatus 139 stores, for example, various types of MR data filled in a k space via the reconstruction function 1413, image data corresponding to the pre-denoise image and the denoise image generated by the noise reduction function 1417, various imaging protocols, and an imaging condition including a plurality of imaging parameters defining each imaging protocol. Specifically, the storage apparatus 139 stores a learned model that is functioned to generate a denoise image in which the noise of the MR image is reduced based on the MR image (the pre-denoise image) generated on the basis of the main scan-MR data and the noise correlation map (the sensitivity map, the g map, or the sensitivity-g map) correlating with the noise included in the MR image. The storage apparatus 139 stores a pre-denoise image 101 and the noise correlation map 102 used for the learned model. The storage apparatus 139 also stores programs corresponding to various types of functions executed in the processing circuitry 141. For example, the storage apparatus 139 stores a program (hereinafter referred to as a noise reduction program) for executing the CNN 105 corresponding to the above-mentioned learned model.

The storage apparatus 139 is, for example, a semiconductor memory element, such as a RAM or a flash memory, a hard disk drive, a solid state drive, or an optical disk. The storage apparatus 139 may also be, for example, a driving device that performs writing and reading of various types of information on a CD-ROM drive, a DVD drive, or a portable memory medium such as a flash memory.

The processing circuitry 141 controls the present medical MRI apparatus 110. The processing circuitry 141 includes the system control function 1411, the reconstruction function 1413, the input function 1415, the noise reduction function 1417, and the correlation data generation function 1419. Various functions performed by the system control function 1411, the reconstruction function 1413, the input function 1415, the noise reduction function 1417, and the correlation data generation function 1419 are stored in the storage apparatus 139 in the form of programs that are executable by a computer. The processing circuitry 141 is a processor that realizes functions corresponding to the respective programs by reading programs corresponding to these various functions from the storage apparatus 139 and executing the read programs. In other words, the processing circuitry 141 in a state where each program is read has the plurality of the functions illustrated in the processing circuit 141 of FIG. 10.

In FIG. 10, it has been described that these various functions are realized by the single processing circuitry 141. However, the functions may be realized in such a manner that the processing circuitry 141 is configured by combining a plurality of independent processors, and each processor executes the program. In other words, each of the above-described functions may be configured as a program, and the single processing circuitry may execute each program, or a specific function may be implemented in dedicated independent program execution circuitry. In the same manner, the couch control circuitry 119, the transmission circuitry 123, the reception circuitry 129, and the imaging control circuitry 131, etc. may also be configured by electronic circuitry such as the above-described processor.

The processing circuitry 141 controls the medical MRI apparatus 110 by the system control function 1411. Specifically, the processing circuitry 141 reads the system control program stored in the storage apparatus 139, loads it in the memory, and controls each circuitry of the present medical MRI apparatus 110 in accordance with the loaded system control program. For example, the processing circuitry 141 reads an imaging protocol from the storage apparatus 139 based on an imaging condition input by the operator via the interface 135. The processing circuitry 141 may generate the imaging protocol based on the imaging condition. The processing circuitry 141 transmits the imaging protocol to the imaging control circuitry 131, and controls imaging on the subject P.

With the reconstruction function 1413, the processing circuitry 141 fills MR data in the readout direction of the k space in accordance with the intensity of the readout gradient magnetic field. The processing circuitry 141 performs a Fourier transform on the MR data filled in the k space to generate an MR image. Specifically, the processing circuitry 141 reconstructs the sensitivity map based on the prescan-MR data regarding the sensitivity map. Based on the prescan-MR data for obtaining a signal-to-noise ratio (hereinafter referred to as an SNR) regarding the calculation of the g-factor, the processing circuitry 141 reconstructs the MR image regarding the SNR (hereinafter referred to as an SNR image). The processing circuitry 141 uses a plurality of the reconstructed SNR images to calculate the g-factor for each pixel. The processing circuitry 141 uses the g-factor corresponding to each of the plurality of pixels to generate the g map. The processing circuitry 141 may also generate the sensitivity-g map by using the sensitivity map and the g map. Furthermore, the processing circuitry 141 may also generate the RF non-transmission map based on a reception signal received by a prescan executed without generating an RF pulse. The processing circuitry 141 may also generate the above-described subtraction image. The above-described sensitivity-g map, RF non-transmission map, and noise correlation map of the generation of the subtraction image, etc. may also be executed by an image processing function (image processor) (unillustrated) in the processing circuitry 141.

The above is the description of the overall configuration of the medical MRI apparatus 110 according to the present embodiment. Hereinafter, the input function 1415 and the noise reduction function 1417 in the present embodiment will be described in detail in the following description of the denoise process.

(Denoise Process)

Figure 11:
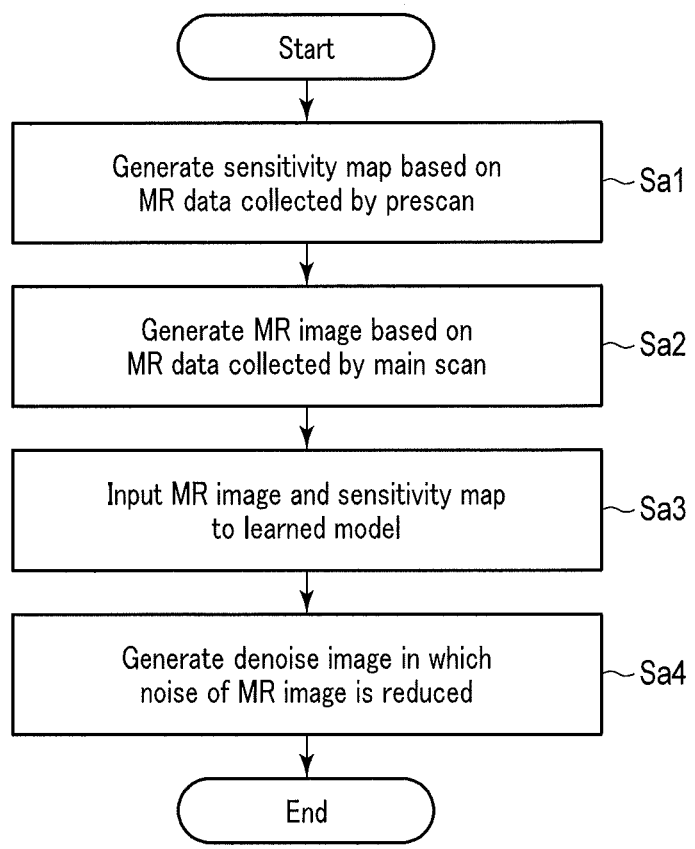
FIG. 11 is a flowchart showing an example of a procedure of a denoise process in the first application example of the present embodiment.

The denoise process in the present application example is a process of generating a denoise image by executing the noise reduction program using the pre-denoise image 101 and the noise correlation map 102. FIG. 11 is a flowchart showing an example of a procedure of the denoise process in the present application example. To provide specific descriptions, the noise correlation map 102 is assumed as being the sensitivity map.

(Step Sa1)

The sensitivity map 102 is generated based on the MR data collected by the prescan. Specifically, the imaging control circuitry 131 executes the prescan with respect to the subject P. The imaging control circuitry 131 outputs the prescan MR data collected by the prescan to the processing circuitry 141. The processing circuitry 141 reconstructs the sensitivity map 102 by executing the Fourier transform on the prescan-MR data by the reconstruction function 1413. Based on the prescan-MR data regarding each of the plurality of receive coils 127 used for parallel imaging, the processing circuitry 141 may generate a plurality of sensitivity maps corresponding to each of the plurality of receive coils 127, and reconstruct the sensitivity map 102 to be input to the input layer 103 by combining the plurality of generated sensitivity maps.

Figure 12:
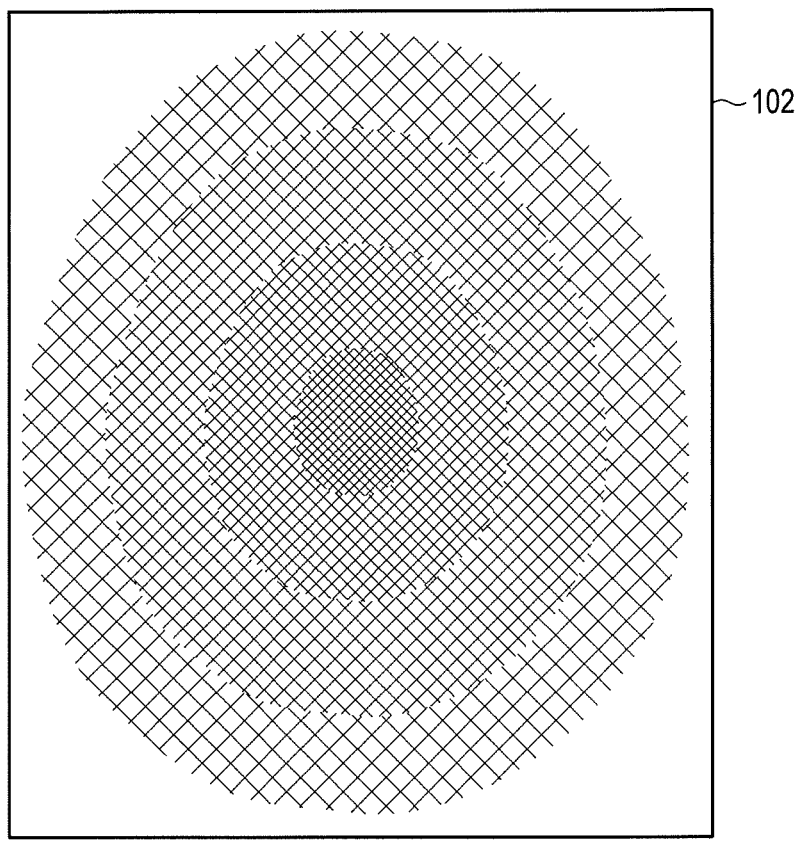
FIG. 12 is a diagram illustrating an example of a sensitivity map generated by a reconstruction function in the first application example of the present embodiment.

FIG. 12 is a diagram illustrating an example of the sensitivity map 102 generated by the reconstruction function 1413. A dense hatching region illustrated in FIG. 12 shows that the sensitivity is low. That is, this shows that the sensitivity is lower as it approaches the center portion of the sensitivity map 102 since it is distant from the receive coil 127. The region with low sensitivity corresponds to a region with relatively more noise in comparison to the region with high sensitivity where the hatching is thin since the signal intensity of the MR signal decreases.

(Step Sa2)

The MR image is generated based on the MR data collected by the main scan. Specifically, the imaging control circuitry 131 executes the main scan with respect to the subject P. The imaging control circuitry 131 outputs the main scan-MR data collected by the main scan to the processing circuitry 141. The processing circuitry 141 reconstructs the MR image as the pre-denoise image 101 by executing the Fourier transform on present main scan-MR data by the reconstruction function 1413.

FIG. 13 is a diagram illustrating an example of the pre-denoise image 101 generated by the reconstruction function 1413. As illustrated in FIG. 13, the center portion of the pre-denoise image 101 is unclear due to noise compared to the peripheral region of the center portion (edge portion).

(Step Sa3)

The MR image, which is the pre-denoise image 101, and the sensitivity map 102 are input to the learned model. Specifically, the processing circuitry 141 inputs the pre-denoise image 101 and the sensitivity map 102 to the input layer 103 by the input function 1415. More specifically, the processing circuitry 141 inputs a plurality of pixel values in the MR image 101 generated by step Sa2 to a plurality of nodes in the first input range 104a of the input layer 103. The processing circuitry 141 inputs a plurality of pixel values in the sensitivity map 102 generated by step Sa1 to a plurality of nodes in the second input range 104b of the input layer 103.

The processing circuitry 141 generates the combination data 104 by combining a plurality of pixel values in the pre-denoise image 101 and a plurality of pixel values in the sensitivity map 102 in the input layer 103 by the noise reduction function 1417. The processing circuitry 141 outputs the combination data 104 to the CNN 105.

In a case where the second modification example is used in the present application example, the processing circuitry 141 inputs the pre-denoise image 101 to the input layer 103, and inputs the sensitivity map 102 to at least one intermediate layer of the CNN 105.

(Step Sa4)

A denoise image 108 in which the noise of the MR image, which is the pre-denoise image 101, is reduced is generated. Specifically, the processing circuitry 141 generates the denoise image 108 by executing the noise reduction program using the pre-denoise image 101 and the noise correlation map 102 by the noise reduction function 1417. The denoise image 108 corresponds to, for example, an image in which the noise in the pre-denoise image 101 is reduced.

In the parallel imaging, in the case of adopting the processes from step Sa1 to step Sa4, the denoise process is preferably executed by using the sensitivity map 102 corresponding to each of the plurality of receive coils and the pre-denoise image 101. Here, the processing circuitry 141 generates the MR image in which the noise is reduced by executing unfolding processing using a plurality of denoise images and a plurality of sensitivity maps corresponding to each of the plurality of receive coils by the reconstruction function 1413. The denoise process regarding the parallel imaging is not limited to the above-described method. Therefore, the denoise image may be generated by using the MR image before the denoise process and after the unfolding processing as the pre-denoise image, and using a map obtained by combining the plurality of sensitivity maps as the noise correlation map.

According to the above-described configuration, the following effects can be obtained.

According to the medical MRI apparatus 110 in the present application example, a learned model that is functioned to generate a denoise image in which the noise of the MR image is reduced based on the medical image (MR image) generated based on the main scan-MR data collected with respect to the subject P and the noise correlation map (the sensitivity map, the g map, or the sensitivity-g map) correlating with the noise included in the medical image is stored, the medical image and the noise correlation map are input to the learned model, and the denoise image in which the noise of the medical image is reduced is generated by using the learned model.

In addition, according to the present medical MRI apparatus 110, it is possible to input the MR image 101 and the noise correlation map 102 to different channels of the input layer 103 in the neural network as the learned model.

In addition, according to the present medical MRI apparatus 110, the MR image is input to the input layer 103 in the neural network as the learned model, and the noise correlation map is input to at least one of the intermediate layers in the neural network. Therefore, since the degree of freedom in which the output changes according to the amount of noise is obtained in the intermediate layer to which the noise correlation map 102 is input, it is possible to reduce noise with an intensity corresponding to the amount of noise for each partial region in the medical image 101.

Furthermore, according to the present medical MRI apparatus 110, the second learned model that is functioned to generate the noise correlation map based on the MR image is stored in the storage apparatus 139, the MR image is input to the second learned model, and the noise correlation map is generated by using the second learned model. Therefore, since the noise correlation map 102 can be generated from the MR image 101 before denoising, there is no need to prepare the noise correlation map 102 separately from the pre-denoise image 101. That is, according to the present medical MRI apparatus 110, since it is unnecessary to collect the image regarding the noise correlation map 102, it is possible to shorten the examination time regarding the generation of the denoise image, and reduce the load with respect to the subject.

(First Modification of First Application Example)

In the present modification, an image corresponding to the noise reduction target image 101 is an intermediate image at the front stage for generating the MR image before denoising (a pre-denoise image), and, for example, is a complex number image.

The processing circuitry 141 generates complex MR data by executing orthogonal phase detection with respect to the collected MR signal by the reconstruction function 1413. The processing circuitry 141 generates the complex number image before denoising by performing a Fourier transform on the complex MR data.

(Denoise Process)

The denoise process in the present modification is a process of generating the denoise image by executing the noise reduction program using the complex number image before denoising and the noise correlation map 102. The denoise image in the present modification corresponds to a denoised complex number image.

The processing circuitry 141 inputs the complex number image, which is the pre-denoise image 101, and the noise correlation map 102 to the input layer 103 of the learned model by the input function 1415. More specifically, the processing circuitry 141 inputs a plurality of pixel values in the complex number image 101 to a plurality of nodes in the first input range 104a of the input layer 103. The processing circuitry 141 inputs a plurality of pixel values in the sensitivity map 102 to a plurality of nodes in the second input range 104b of the input layer 103.

The processing circuitry 141 generates the denoise image 108 by executing the noise reduction program using the complex number image 101 before denoising and the noise correlation map 102 by the noise reduction function 1417. The denoise image 108 corresponds to, for example, an image in which the noise in the complex number image 101 is reduced.

The processing circuitry 141 generates the MR image by using the denoised complex number image 101. In the present modification, since the processing contents regarding the first modification example and the second modification example can be understood by replacing the noise reduction target image 101 with the complex number image before denoising, descriptions thereof will be omitted.

According to the configurations mentioned above, the following effects may be obtained.

According to the medical MRI apparatus 110 in the present modification, the noise correlation map and the intermediate image are input to the learned model that is functioned to generate a denoise image (denoised complex number image) in which the noise of the intermediate image is reduced based on the intermediate image generated based on the data collected with respect to the subject (complex number image before denoising) and the noise correlation map (the sensitivity map, the g map, or the sensitivity-g map) correlating with the noise included in the intermediate image, and the denoise image in which the noise of the intermediate image is reduced can be generated. Explanations on other advantageous effects will be omitted since they are similar to those of the first application example.

(Second Modification of First Application Example)

The noise correlation map 102 used in the present modification is a map (hereinafter referred to as a combined map) generated by using at least one of the sensitivity map, the g map, a static magnetic field inhomogeneity map showing inhomogeneity of a static magnetic field, a gradient magnetic field inhomogeneity map showing inhomogeneity of a gradient magnetic field, and a density map corresponding to density of data in k-space, or at least two among the sensitivity map, the g map, the static magnetic field inhomogeneity map, the gradient magnetic field inhomogeneity map, and the density map. Hereinafter, the static magnetic field inhomogeneity map, the gradient magnetic field inhomogeneity map, the density map, and the combined map will be described.

The imaging control circuitry 131 executes shimming imaging in the prescan. The imaging control circuitry 131 collects an MR signal (hereinafter referred to as a shimming MR signal) by the shimming imaging.

The processing circuitry 141 generates static field distribution based on the shimming MR signal. The processing circuitry 141 calculates various shimming values regarding the execution of static magnetic field shimming by using the static field distribution. The processing circuitry 141 executes the static magnetic field shimming by using the calculated shimming value. The processing circuitry 141 calculates the static field distribution after the static magnetic field shimming by using the calculated shimming value. The static field distribution after the static magnetic field shimming shows inhomogeneity of the static magnetic field. The static magnetic field inhomogeneity map corresponds to the static field distribution after the static magnetic field, shimming.

The storage apparatus 139 stores a correction value (hereinafter referred to as a distortion correction value) that is used for gradient distortion correction (hereinafter referred to as GDC) with respect to an MR image, and that is in accordance with the distance from the center of the magnetic field in an imaging region. The distortion correction value corresponds to a deviation amount from the linearity (a designed value) of the gradient magnetic field on the basis of the center of the magnetic field. The distribution of the distortion correction value in the imaging region indicates the inhomogeneity of the gradient magnetic field. The gradient magnetic field inhomogeneity map corresponds to the distribution of the distortion correction value. The static magnetic field inhomogeneity map and the gradient magnetic field inhomogeneity map are stored in the storage apparatus 139.

The processing circuitry 141 generates the density map by performing a Fourier transform on data in the k-space by the reconstruction function 1413. The density map is a map that corresponds to the density of data in the k-space. The data in the k-space is, for example, data obtained by a collection that does not sample the k-space homogeneously, such as a radial collection or a spiral collection, or under sampling data obtained by a cartesian collection that is inhomogeneous in the k-space. Since the processing of re-gridding is applied to these data before the Fourier transform, the density map becomes a map that reflects inhomogeneous noise.

The processing circuitry 141 may also generate the combined map obtained by combining these maps by using at least two maps among the sensitivity map, the g map, the static magnetic field inhomogeneity map, the gradient magnetic field inhomogeneity map, and the density map. For example, in the case where the sensitivity map and the g map are combined, the combined map corresponds to the above-mentioned sensitivity-g map. Here, the combined map has characteristics of the sensitivity map and the g map. At least one of the sensitivity map, the g map, the static magnetic field inhomogeneity map, the gradient magnetic field inhomogeneity map, and the density map, or the combined map is used as the noise correlation map 102.

In the case where a plurality of noise correlation maps are input to the input layer 103, the processing circuitry 141 inputs the plurality of noise correlation maps to a preset channel. The channel to which each of the plurality of noise correlation maps is input is set when learning the machine learning model.

According to the configurations mentioned above, the following effects may be obtained.

According to the medical MRI apparatus 110 in the present modification, as the noise correlation map, a map generated by using at least one of the sensitivity map, the g map, the static magnetic field inhomogeneity map showing the inhomogeneity of the static magnetic field, the gradient magnetic field inhomogeneity map showing or the inhomogeneity of the gradient magnetic field, and the density map corresponding to density of data in k-space, or at least two among the sensitivity map, the g map, the static magnetic field inhomogeneity map, the gradient magnetic field inhomogeneity map, and the density map may be used. Explanations on other advantageous effects will be omitted since they are similar to those of the first application example.

(Second Application Example)

The medical image diagnostic apparatus in the present application example is a medical X-ray CT apparatus on which the processing circuitry 141 in the present embodiment is mounted. In the present application example, the medical image corresponding to the noise reduction target image 101 corresponds to an image before the denoise process by the noise reduction function 1417 in FIG. 1, and an X-ray CT image reconstructed based on the pre-processed projection data generated with respect to the CT scan on the subject P (hereinafter referred to as a pre-denoise CT image). Furthermore, the intermediate image corresponding to the noise reduction target image 101 corresponds to a sinogram generated based on the projection data (hereinafter referred to as a pre-denoise sinogram).

In addition, in the present application example, when the noise reduction target image 101 input to the input layer 103 is the pre-denoise sinogram, the noise correlation map 102 corresponds to, in the pre-denoise CT image, a map (hereinafter referred to as a transmission length map) showing the transmission length of the subject P along the ray of X-rays passing through the subject P for each view. The transmission length map corresponds to data in which the transmission length along the ray of X-rays incident on an X-ray detecting element from the focal point where the X-rays are generated in an X-ray tube is arranged, for example, by setting the number of views as the vertical axis and setting the element numbers of a plurality of X-ray detecting elements arranged in the channel direction as the horizontal axis. Hereinafter, for the sake of concrete explanation, it is assumed that the element numbers are 1 to M (M is a natural number). The noise correlation map 102 is not limited to the transmission length map, and may be any image as long as the image is correlated with the amount of noise in the CT image.

In addition, in the present application example, when the noise reduction target image 101 input to the input layer 103 is the pre-denoise CT image, the noise correlation map 102 corresponds to an image reconstructed using the transmission length map (hereinafter referred to as a transmission length reconstruction image).

In the present application example, processing contents in the case of performing denoise using the pre-denoise CT image will be described later. In addition, in the present application example, since the processing contents related to the first application example and the second application example can be understood by replacing the noise reduction target image 101 with the pre-denoise sinogram and replacing the noise correlation map 102 with the transmission length map, descriptions thereof will be omitted.

As for the medical X-ray CT apparatus, there are various types such as a third generation CT and a fourth generation CT. Any type is applicable to the present application example. Here, the third generation CT is a rotate/rotate-type in which the X-ray tube and the detector rotate integrally around the subject. The fourth generation CT is a stationary/rotate-type in which a plurality of ring-like arrayed X-ray detecting elements are fixed, and only the X-ray tube rotates around the subject.

Figure 14:
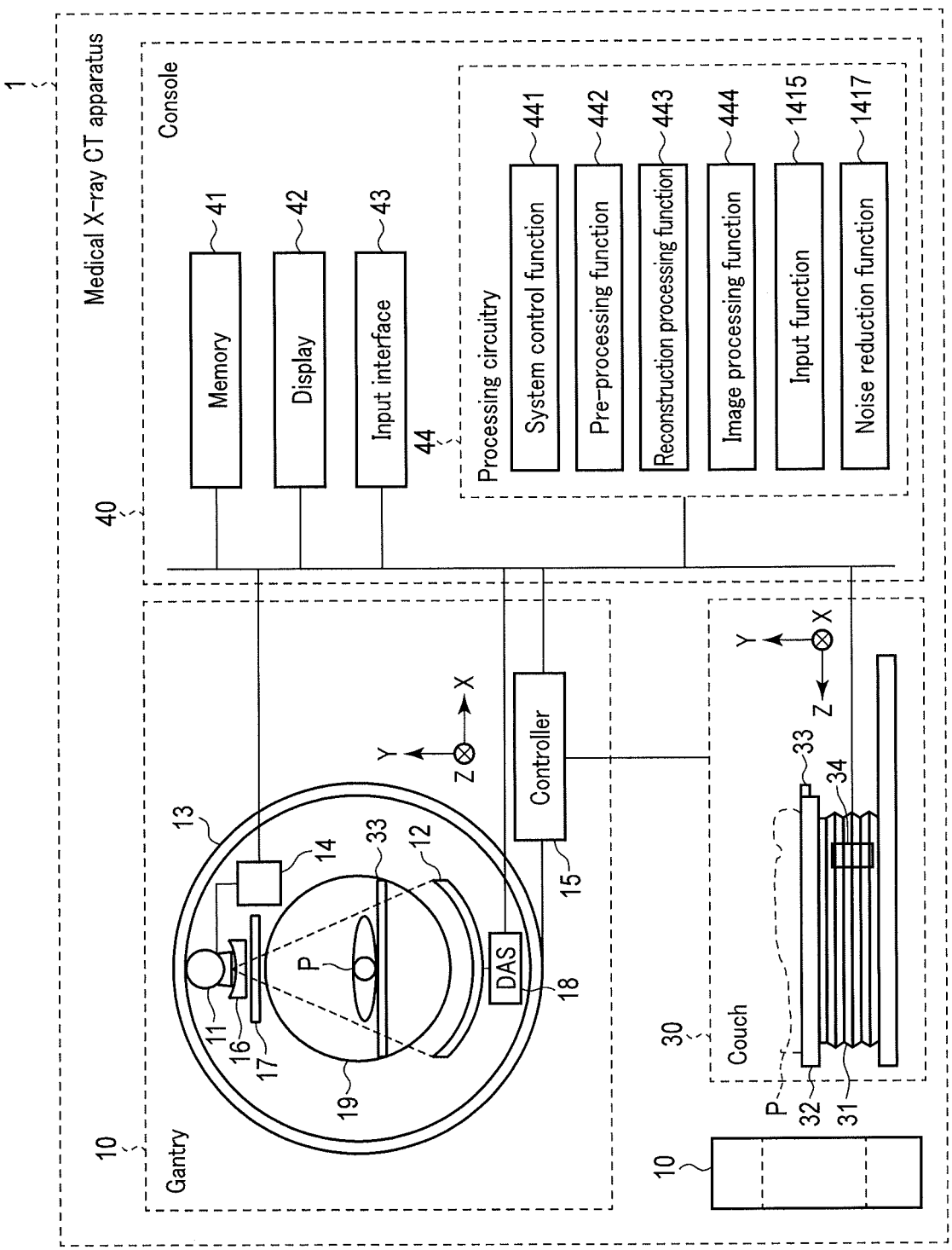
FIG. 14 is a diagram illustrating an example of a configuration of a medical X-ray CT apparatus in a second application example of the present embodiment.

FIG. 14 is a diagram illustrating a configuration of a medical X-ray CT apparatus 1 according to the present application example. The medical X-ray CT apparatus 1 emits X-rays to the subject P from an X-ray tube 11, and detects the emitted X-rays by an X-ray detector 12. The medical X-ray CT apparatus 1 generates the pre-denoise CT image regarding the subject P based on the output from the X-ray detector 12.

As illustrated in FIG. 14, the medical X-ray CT apparatus 1 includes a gantry 10, a couch 30, and a console 40. In FIG. 14, for convenience of explanation, a plurality of gantries 10 are illustrated. The gantry 10 is a scanning apparatus having a configuration for performing X-ray CT imaging on the subject P. The couch 30 is a conveyor for placing the subject P to be the target of the X-ray CT imaging thereon, and positioning the subject P. The console 40 is a computer that controls the gantry 10. For example, the gantry 10 and the couch 30 are installed in a CT examination room, and the console 40 is installed in a control room adjacent to the CT examination room. The gantry 10, the couch 30, and the console 40 are connected in a wired or wireless manner to be communicable with each other. The console 40 does not necessarily have to be installed in the control room. For example, the console 40 may be installed in the same room as the gantry 10 and the couch 30. The console 40 may also be embedded in the gantry 10.

As illustrated in FIG. 14, the gantry 10 includes the X-ray tube 11, the X-ray detector 12, a rotation frame 13, an X-ray high voltage apparatus 14, a controller 15, a wedge 16, a collimator 17, and data acquisition system (DAS) 18.

The X-ray tube 11 emits X-rays to the subject P. Specifically, the X-ray tube 11 includes a cathode for generating thermal electrons, an anode for receiving thermal electrons emitted from the cathode to generate X-rays, and a vacuum tube for holding the cathode and the anode. The X-ray tube 11 is connected to the X-ray high voltage apparatus 14 via a high voltage cable. A tube voltage is applied between the cathode and the anode by the X-ray high voltage apparatus 14. By applying the tube voltage, thermal electrons are emitted from the cathode toward the anode. Tube current flows as thermal electrons are emitted from the cathode to the anode. By applying a high voltage from the X-ray high voltage apparatus 14 and supplying a filament current, thermal electrons are emitted from the cathode (filament) to the anode (target), thereby generating X-rays by colliding the thermal electrons against the anode. For example, for the X-ray tube 11, there is a rotary anode type X-ray tube that generates X-rays by irradiating a rotating anode with thermal electrons.

Hardware for generating the X-rays is not limited to the X-ray tube 11. For example, X-rays may be generated by using a fifth generation system instead of the X-ray tube 11. The fifth generation system includes a focus coil that converges electron beams generated from an electron gun, a deflection coil that causes electromagnetic deflection, and a target ring that surrounds half of a circumference of the subject P and generates X-rays by colliding the deflected electron beams.

The X-ray detector 12 detects X-rays emitted from the X-ray tube 11 and passing through the subject P, and outputs an electric signal corresponding to the detected X-ray dose to the DAS 18. The X-ray detector 12 has a structure in which a plurality of X-ray detecting element arrays in which a plurality of X-ray detecting elements are arranged in the channel direction are arranged in the slice direction (a column direction). The X-ray detector 12 is, for example, an indirect conversion type detector having a grid, a scintillator array, and a photosensor array. The scintillator array has a plurality of scintillators. The scintillator has a scintillator crystal that outputs light in a light quantity in accordance with an incident X-ray dose. The grid is arranged on an X-ray incident surface side of the scintillator, and has an X-ray shielding plate that absorbs scattered X-rays. The grid may sometimes be referred to as a collimator (a one-dimensional collimator or a two-dimensional collimator). The photosensor array has a function for performing conversion to obtain an electric signal in accordance with the quantity of light from the scintillator. As the photosensor, for example, a photodiode or a photomultiplier is used. The X-ray detector 12 may be a direct conversion type detector having a semiconductor element for converting incident X-rays into electric signals. The X-ray detector is an example of an X-ray detection unit.

The rotation frame 13 is an annular frame that rotatably supports the X-ray tube 11 and the X-ray detector 12 around a rotation axis (Z-axis). Specifically, the rotation frame 13 supports the X-ray tube 11 and the X-ray detector 12 on opposite sides. The rotation frame 13 is rotatably supported around the rotation axis on a fixed frame (unillustrated). The rotation frame 13 is rotated around the rotation axis by the controller 15. In this manner, the rotation frame 13 rotates the X-ray tube 11 and the X-ray detector 12 around the rotation axis. The rotation frame 13 rotates around the rotation axis at a certain angular velocity by receiving power from a drive mechanism of the controller 15. An image field of view (FOV) is set in a bore 19 of the rotation frame 13. Furthermore, the rotation frame 13 is an example of a rotation unit.

In the present application example, the rotation axis of the rotation frame 13 or the longitudinal direction of the couch top 33 of the couch 30 in a non-tilted state is defined as the Z-axis direction, an axial direction that is orthogonal to the Z-axis direction and is horizontal to the floor is defined as the X-axis direction, and an axial direction that is orthogonal to the Z-axis direction and vertical to the floor is defined as the Y-axis direction.

The X-ray high voltage apparatus 14 includes a high voltage generator and an X-ray controller. The high voltage generator includes electric circuitry such as a transformer and a rectifier. The high voltage generator generates a high voltage to be applied to the X-ray tube 11, and a filament current to be supplied to the X-ray tube 11. The X-ray controller controls the output voltage in accordance with the X-ray to be emitted by the X-ray tube 11. The high voltage generator may be a transformer system or an inverter system. Furthermore, the X-ray high voltage apparatus 14 may be provided on the rotation frame 13 inside the gantry 10, or may be provided on a fixed frame (unillustrated) inside the gantry 10. The X-ray high voltage apparatus 14 is an example of an X-ray high voltage unit.

The wedge 16 is a filter for adjusting the X-ray dose to be irradiated on the subject P. Specifically, the wedge 16 attenuates the X-rays so that the X-ray dose to be emitted from the X-ray tube 11 to the subject P becomes a predetermined distribution. As the wedge 16, for example, an aluminum metallic plate such as a wedge filter or a bow-tie filter is used. The metallic plate is processed in advance so as to have a predetermined target angle or a predetermined thickness.

The collimator 17 limits the irradiation range of the X-rays passing through the wedge 16. The collimator 17 slidably supports a plurality of lead plates that shield the X-rays. The collimator 17 adjusts the formation of the slits that are formed by the plurality of lead plates. In some cases, the collimator 17 is referred to as an X-ray diaphragm.

The DAS 18 reads the electric signal in accordance with the X-ray dose detected by the X-ray detector 12 from the X-ray detector 12. The DAS 18 amplifies the read electric signal. By integrating the amplified electric signal over a view period, the DAS 18 collects detection data having digital values corresponding to the X-ray dose over the view period. The DAS 18 is realized by, for example, an application specific integrated circuit (ASIC) on which circuit elements that are capable of generating the detection data are mounted. The detection data is transferred to the console 40 via a non-contact data transmission apparatus, etc. The non-contact data transmission apparatus includes a transmitter provided on the rotation frame 13 and a receiver provided on a non-rotating portion of the gantry 10 (for example, an unillustrated fixed frame). The transmitter includes a light-emitting diode (LED). The receiver includes a photodiode. The transmitter transmits the detection data to the receiver via the light-emitting diode. The receiver receives the detection data via the photo-diode. The receiver transmits the received detection data to the console 40. In this manner, the non-contact data transmission apparatus transmits the detection data to the console via optical communication. The transmission method of the detection data from the rotation frame 13 to the non-rotating portion of the gantry 10 is not limited to the above-mentioned optical communication, and may adopt any system as long as it is non-contact type data transmission.

The controller 15 controls the X-ray high voltage apparatus 14 and the DAS 18 in order to execute X-ray CT imaging in accordance with the system control function 441 in the processing circuitry 44 of the console 40. The controller 15 includes processing circuitry having a CPU or an MPU, and a drive mechanism, such as a motor and an actuator. The processing circuitry 44 includes a processor, such as a CPU, and a memory, such as a ROM or a RAM, as hardware resources. The controller 15 may also be realized by an ASIC or a field programmable gate array. The controller 15 may also be realized by other complex programmable logic devices or simple programmable logic devices. The controller 15 has a function of performing operation control of the gantry 10 and the couch 30 by receiving input signals from the console 40 or an input interface 43 attached to the gantry 10, which will be explained later. For example, the controller 15 receives the input signals and controls rotation of the rotation frame 13, controls tilting of the gantry 10, and controls operation of the couch 30 and the couch top 33. The control of tilting the gantry 10 is realized by the controller 15 rotating the rotation frame 13 about an axis parallel to the X-axis direction by tilt angle information input by the input interface 43 attached to the gantry 10. The controller 15 may be provided on the gantry 10, or may be provided on the console 40. The controller 15 is an example of a gantry control unit.

The couch 30 comprises a base 31, a supporting frame 32, the couch top 33, and a couch driving apparatus 34. The base 31 is installed on the floor of the CT examination room. The base 31 is a housing that supports the supporting frame 32 movably in a vertical direction (Y-axis direction) with respect to the floor. The supporting frame 32 is a frame provided on the upper portion of the base 31. The supporting frame 32 supports the couch top 33 slidably along the central axis (Z-axis). The couch top 33 is a plate that has flexibility, and on which the subject P is placed.

The couch driving apparatus 34 is accommodated inside the housing of the bed 30. The couch driving apparatus 34 is a motor or an actuator that generates power for moving the supporting frame 32 and the couch top 33 on which the subject P is placed. The couch driving apparatus 34 operates in accordance with the control by the console 40, etc. In addition to the couch top 33, the couch driving apparatus 34 may also move the supporting frame 32 in the longitudinal direction of the couch top 33.

The console 40 includes the memory 41, the display 42, the input interface 43, and the processing circuitry 44. Data communication among the memory 41, the display 42, the input interface 43, and the processing circuitry 44 is carried out via a bus (BUS). Although the console 40 is explained as a separate body from the gantry 10, the console 40 or a part of each constituent element of the console 40 may be included in the gantry 10. In the present application example, in the case where the noise correlation map is generated from the pre-denoise image as described in the first modification example, the processing circuitry 44 in the medical X-ray CT apparatus 1 further includes a correlation data generation function as illustrated in FIG. 6.

The memory 41 is a storage apparatus such as HDD, SSD, integrated circuit storage device, or the like for storing a variety of information. The memory 41 stores, for example, the projection data generated by the pre-processing function 442 or data of the pre-denoise CT image generated by the reconstruction processing function 443, data of the denoise image (hereinafter referred to as a denoise sinogram) 108 generated by the noise reduction function 1417, and the like. In the present application example, the denoise sinogram corresponds to the denoise image 108. In addition, the memory 41 stores the learned model that is functioned to generate the denoise sinogram 108 with noise reduced in the pre-denoise sinogram 101, based on the pre-denoise sinogram 101 and a transmission length map 102. The memory 41 stores the transmission length map 102 used for the learned model. The memory 41 stores the CT image reconstructed based on the denoise sinogram 108 (hereinafter referred to as a denoise CT image). In addition, the memory 41 stores programs corresponding to various functions to be executed in the processing circuit 44. For example, the memory 41 stores a noise reduction program for performing the CNN 105 corresponding to the above-described learned model.

The memory 41 may be a portable storage medium such as a compact disc (CD), a digital versatile disc (DVD), or a flash memory, in addition to the HDD, the SSD, or the like. The memory 41 may be a driving apparatus that reads and writes a variety of information with a semiconductor memory element such as a flash memory or a RAM. Furthermore, a storage region of the memory 41 may be inside the medical X-ray CT apparatus 1, or inside an external storage apparatus connected to the network.

The display 42 displays a variety of information. For example, the display 42 outputs the denoise CT image generated by the reconstruction processing function 443 in the processing circuitry 44, graphical user interface (GUI) for receiving various operations from the operator, and the like. As the display 42, various arbitrary displays can be appropriately used. For example, a liquid crystal display, a CRT display, an organic EL display, or a plasma display can be used as the display 42. The display 42 may also be provided on the gantry 10. In addition, the display 42 may be a desktop type display, or may be constituted by a tablet terminal or the like capable of wireless communication with the main body of the console 40.

The input interface 43 receives various input operations from the operator, converts the received input operation into an electric signal, and outputs the electric signal to the processing circuitry 44. For example, the input interface 43 receives, from the operator, a collection condition for collecting projection data, a reconstruction condition for reconstructing the denoise CT image and the pre-denoise CT image, an image processing condition for generating the post-processing image from the denoise CT image, and the like. As the input interface 43, for example, a mouse, a keyboard, a trackball, a switch, a button, a joystick, a touch pad, a touch panel display, and the like can be used as appropriate. In the present application example, the input interface 43 is not limited to those having physical operation parts such as a mouse, a keyboard, a trackball, a switch, a button, a joystick, a touch pad, and a touch panel display. For example, an electric signal processing circuitry that receives an electric signal corresponding to an input operation from an external input device provided separately from the apparatus, and outputs the electric signal to the processing circuitry 44 is also included as an example of the input interface 43. The input interface 43 may also be provided on the gantry 10. In addition, the input interface 43 may be configured by a tablet terminal or the like capable of performing wireless communication with the main body of the console 40.

The processing circuitry 44 controls the operation of the entire medical X-ray CT apparatus 1 according to the electric signal of the input operation output from the input interface 43. For example, the processing circuitry 44 includes, as a hardware resource, a processor such as a CPU, an MPU, a GPU, and a memory such as a ROM and a RAM. The processing circuitry 44 executes the system control function 441, the pre-processing function 442, the reconstruction processing function 443, the image processing function 444, the input function 1415, the noise reduction function 1417, and the like by a processor that executes a program loaded into a memory. The plurality of functions are not limited to the case where they are realized by single processing circuitry. A plurality of independent processors may be combined to form the processing circuitry, and to realize the plurality of functions by each of the processors executing a program.

The processing circuitry 44 controls the X-ray high voltage apparatus 14, the controller 15, and the DAS 18 in order to perform an X-ray CT imaging by the system control function 441. The processing circuitry 44 that executes the system control function 441 is an example of a system control unit.

The processing circuitry 44 performs a logarithmic transforming process on the detection data output from the DAS 18, an offset correction process, a sensitivity correction process between channels, and pre-processing such as beam hardening correction by the pre-processing function 442. Therefore, the processing circuitry 44 generates projection data corresponding to each of a plurality of view angles. In some cases, data prior to pre-processing (detection data) and data after pre-processing may collectively be referred to as projection data. The processing circuitry 44 generates a sinogram by using the projection data over the view angles. The generation of the sinogram may be performed by the reconstruction processing function 443. The processing circuitry 44 that executes the pre-processing function 442 is an example of a pre-processing unit.

The processing circuity 44 performs the reconstruction processing on the projection data after pre-processing and before denoise process by using a filter corrected back projection method, a successive approximation reconstruction method, or the like by the reconstruction processing function 443, and generates data of the pre-denoise CT image. In addition, the processing circuitry 44 performs the reconstruction processing on the denoise sinogram 108 corresponding to the denoise image, and generates data of the denoise CT image. The processing circuitry 44 that executes the reconstruction processing function 443 is an example of a reconstruction processing unit.

The processing circuitry 44 converts the data of the denoise CT image generated by the noise reduction function 1417 into sectional image data of an arbitrary section or rendering image data of an arbitrary viewpoint direction by the image processing function 444. The conversion is performed based on the input operation received from the operator via the input interface 43. For example, the processing circuitry 44 generates rendering image data in an arbitrary viewpoint direction by performing three-dimensional image processing such as volume rendering to the data of the denoise CT image, surface volume rendering, image value projection processing, multi-planer reconstruction (MPR) processing, or curved MPR (CPR) processing. The reconstruction processing function 443 may directly generate the rendering image data in the arbitrary viewpoint direction.

The console 40 has been explained as executing a plurality of the functions by a single console; however, the functions may be executed by separate consoles. For example, the functions of the processing circuitry 44, such as the pre-processing function 442 and the reconstruction processing function 443, may be separated.

The processing circuitry 44 is not limited to the case of being included in the console 40, and may be included in an integrated server that collectively performs processing on the detection data acquired by a plurality of medical image diagnostic apparatuses.

The post-processing may be performed by the console 40 or an external work station. The post-processing may also be performed simultaneously by both the console 40 and the work station.

The technique according to the present application example can be applied to a single-tube-bulb type medical X-ray CT apparatus, or a so-called multi-tube-bulb type medical X-ray CT apparatus that has a plurality of pairs of X-ray tubes and detectors mounted on a rotational ring.

The overall configuration of the medical X-ray CT apparatus 1 according to the present application example has been described. Hereinafter, the input function 1415 and the noise reduction function 1417 in the present application example will be described in detail in the following description of the denoise process.

(Denoise Process)

Figure 15:
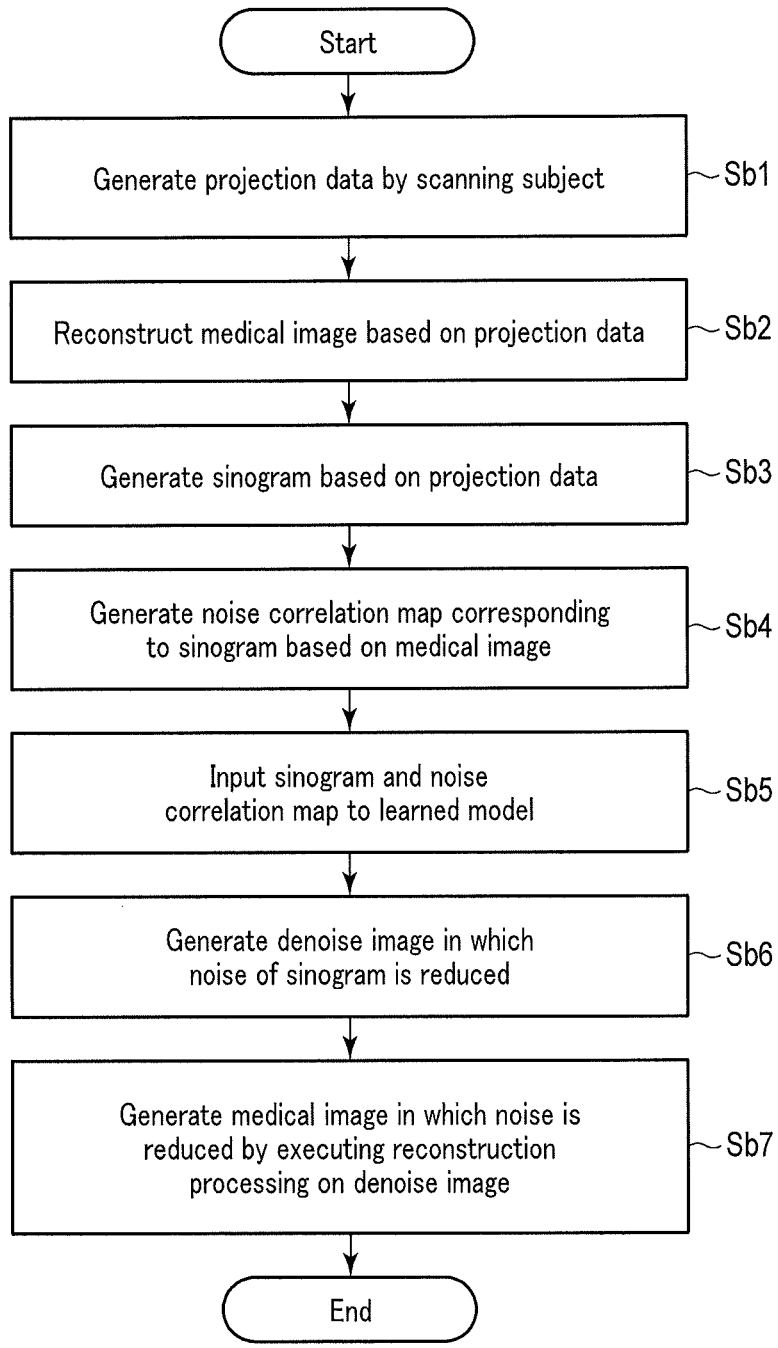
FIG. 15 is a flowchart showing an example of a procedure of a denoise process in the second application example of the present embodiment.

The denoise process in the present application example is a process of generating the denoise sinogram 108 by executing the noise reduction program using the pre-denoise sinogram 101 and the transmission length map 102. FIG. 15 is a flowchart showing an example of a procedure of the denoise process in the present application example.

(Step Sb1)

The projection data is generated by performing a CT scan on the subject P. Specifically, the processing circuitry 44 generates the projection data by performing pre-processing on the detection data output from the DAS 18 by the pre-processing function 442.

(Step Sb2)

The medical image is reconstructed based on the projection data. Specifically, the processing circuitry 44 reconstructs the pre-denoise CT image by performing reconstruction processing on the projection data by the reconstruction processing function 443.

(Step Sb3)

The sinogram is generated based on the projection data. Specifically, the processing circuitry 44 generates the pre-denoise sinogram 101 by using the projection data over the plurality of view angles in the CT scan performed on the subject P by the pre-processing function 442.

FIG. 16 is a diagram illustrating an example of the pre-denoise sinogram 101. As illustrated in FIG. 16, the pre-denoise sinogram 101 is generated by setting the number of views as the vertical axis and the element numbers of a plurality of X-ray detecting elements arranged in the channel direction as the horizontal axis, and arranging the projection data corresponded to the number of views and the element numbers. As illustrated in FIG. 16, the pre-denoise sinogram 101 is unclear due to noise.

(Step Sb4)

The noise correlation map corresponding to the pre-denoise sinogram 101 is generated based on the medical image. Specifically, the processing circuitry 44 calculates a transmission length along the ray of the X-rays incident on each of the plurality of X-ray detecting elements in each of the plurality of view angles using the pre-denoise CT image by the image processing function 444. By arranging the transmission length corresponded to each of the plurality of view angles and each of the plurality of element numbers along the view angles and the element numbers, the processing circuitry 44 generates the transmission length map 102 as the noise correlation map. The transmission length map 102 may also be generated by other functions in the processing circuitry 44.

FIG. 17 is a diagram illustrating an example of the plurality of transmission lengths corresponding to each of the plurality of element numbers at a view angle of 0°. As illustrated in the pre-denoise CT image BdnCT in FIG. 17, a ray r1 of an X-ray directed to an element number ch1 from a focal point TF passes through the subject P at a transmission length L1. Similarly, rays r2, r3, and rM of the X-rays directed to element numbers ch2 and ch3 from the focal point TF pass through the subject P at transmission lengths L2, L3, and LM, respectively.

FIG. 18 is a diagram illustrating an example of the transmission length map 102. As illustrated in FIG. 18, the transmission length map 102 is an image in which the transmission lengths are arranged, for example, by setting the number of views as the vertical axis and the element numbers as the horizontal axis.

(Step Sb5)

The pre-denoise sinogram 101 and the transmission length map 102 are input to the learned model. Specifically, the processing circuitry 44 inputs the pre-denoise sinogram 101 and the transmission length map 102 to the input layer 103 by the input function 1415. More specifically, the processing circuitry 44 inputs a plurality of pixel values in the pre-denoise sinogram 101, which is generated in step Sb3, to a plurality of nodes in the first input range 104a of the input layer 103. The processing circuitry 44 inputs a plurality of pixel values in the transmission length map 102, which is generated in step Sb4, to a plurality of nodes in the second input range 104b of the input layer 103.

The processing circuitry 44 generates the combination data 104 by combining a plurality of pixel values in the pre-denoise sinogram 101 and a plurality of pixel values in the transmission length map 102 in the input layer 103 by the noise reduction function 1417. The processing circuitry 141 outputs the combination data 104 to the CNN 105.

In a case where the second modification example is used in the present application example, the processing circuitry 44 inputs the pre-denoise sinogram 101 to the input layer 103 and inputs the transmission length map 102 to at least one intermediate layer of the CNN 105.

(Step Sb6)

A denoise image with reduced sinogram noise is generated. Specifically, the processing circuitry 44 generates the denoise sinogram 108 by executing the noise reduction program using the pre-denoise sinogram 101 and the transmission length map 102 by the noise reduction function 1417. The denoise sinogram 108 is an image with reduced noise in the pre-denoise sinogram 101.

(Step Sb7)

A medical image with reduced noise is generated by performing reconstruction processing on the denoise sinogram 108, which is the denoise image. Specifically, the processing circuitry 44 reconstructs the denoise CT image by performing the reconstruction processing on the denoise sinogram 108 by the reconstruction processing function 443.

Figure 19:
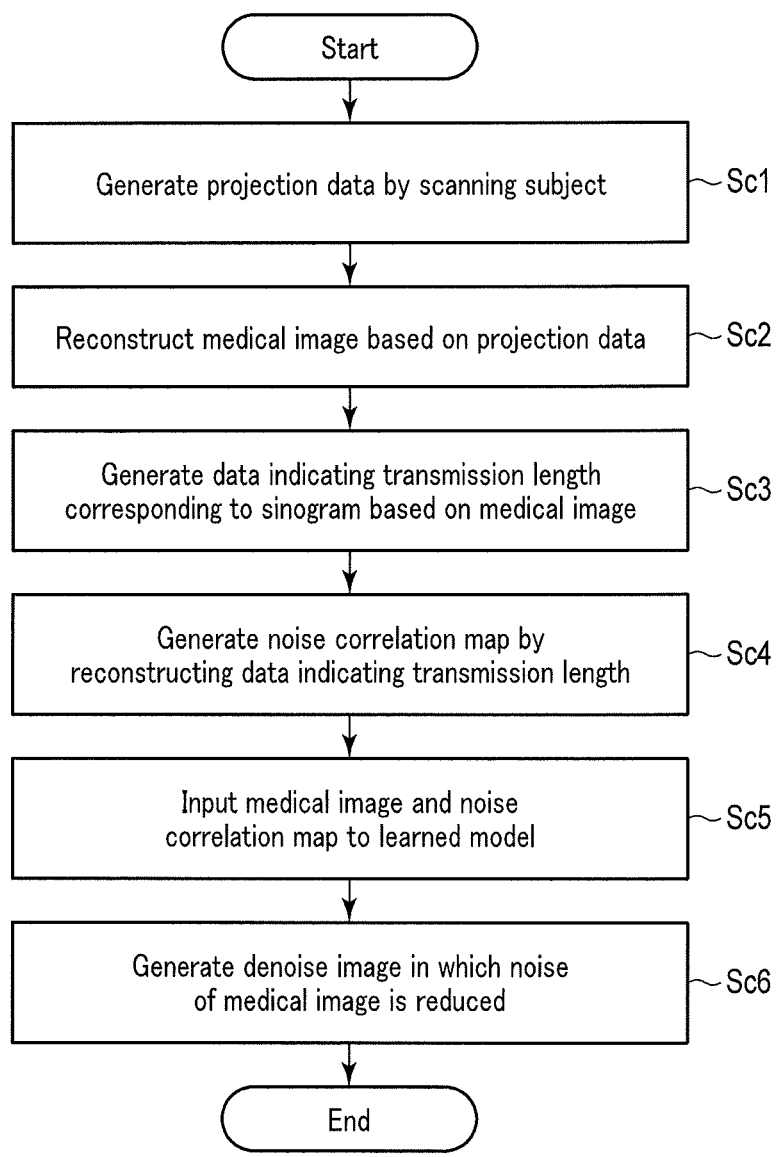
FIG. 19 is a flowchart showing an example of a procedure of a denoise process in a modification of the second application example of the present embodiment.

Hereinafter, as the modification of the present application example, the denoise process in the case of using the pre-denoise CT image as the medical image 101 will be described. FIG. 19 is a flowchart showing an example of a procedure of the denoise process in the modification of the present application example. Since Steps Sc1 and Sc2 are the same process as Step Sb1 and Sb2, descriptions thereof will be omitted.

(Step Sc3)

Data indicating the transmission length corresponding to the pre-denoise sinogram is generated based on the medical image. The data indicating the transmission length corresponds to the transmission length map illustrated in FIG. 18.

(Step Sc4)

A noise correlation map is generated by reconstructing the data indicating the transmission length. Specifically, the processing circuitry 44 generates the transmission length reconstruction image by performing the reconstruction processing on the data indicating the transmission length by the reconstruction processing function 443. The transmission length reconstruction image corresponds to the noise correlation map 102.

(Step Sc5)

The pre-denoise CT image 101 and the transmission length reconstruction image 102 are input to the learned model. Specifically, the processing circuitry 44 inputs the pre-denoise CT image 101 and the transmission length reconstruction image 102 to the input layer 103 by the input function 1415. More specifically, the processing circuitry 44 inputs a plurality of pixel values in the pre-denoise reconstruction image 101, which is generated in step Sc2, to a plurality of nodes in the first input range 104a of the input layer 103. The processing circuitry 44 inputs a plurality of pixel values in the transmission length reconstruction image 102, which is generated in step Sc4, to a plurality of nodes in the second input range 104b of the input layer 103.

The processing circuitry 44 generates the combination data 104 by combining a plurality of pixel values in the pre-denoise CT image 101 and a plurality of pixel values in the transmission length reconstruction image 102 in the input layer 103 by the noise reduction function 1417. The processing circuitry 141 outputs the combination data 104 to the CNN 105.

In a case where the second modification example is used in the present application example, the processing circuitry 44 inputs the pre-denoise CT image 101 to the input layer 103 and inputs the transmission length reconstruction image 102 to at least one intermediate layer of the CNN 105.

(Step Sc6)

A denoise image 108 in which the noise of the pre-denoise CT image 101 is reduced is generated. The denoise image corresponds to the denoise CT image. Specifically, the processing circuitry 44 generates the denoise CT image 108 by executing the noise reduction program using the pre-denoise CT image 101 and the transmission length reconstruction image 102 by the noise reduction function 1417.

According to the configurations mentioned above, the following effects can be obtained.

According to the medical X-ray CT apparatus 1 of the present application example, it is possible to store the learned model functioned to generate the denoise image, in which the noise of the medical image or the noise of the intermediate image is reduced, based on the medical image (pre-denoise CT image) generated based on the projection data collected with respect to the subject P, the intermediate image (pre-denoise sinogram) at the front stage for generating the medical image, and the noise correlation map (transmission length map or transmission length reconstruction image) correlated with noise included in the medical image or the intermediate image, input the medical image or the intermediate image and the noise correlation map to the learned model, and generate the denoise image, in which the noise of the medical image or the noise of the intermediate image is reduced, by using the learned model.

In addition, according to the present medical X-ray CT apparatus 1, the pre-denoise CT image or the pre-denoise sinogram and the noise correlation map 102 can be input to mutually different channels of the input layer 103 in the neural network as the learned model.

In addition, according to the present medical X-ray CT apparatus 1, the pre-denoise CT image or the pre-denoise sinogram can be input to the input layer 103 of the neural network as the learned model, and the noise correlation map can be input to at least one of the plurality of intermediate layers in the neural network. Therefore, since the degree of freedom in which the output changes according to the amount of noise is obtained in the intermediate layer to which the noise correlation map 102 is input, it is possible to reduce noise with an intensity corresponding to the amount of noise for each partial region in the pre-denoise CT image or the pre-denoise sinogram 101.

Furthermore, according to the present medical X-ray CT apparatus 1, it is possible to store the second learned model functioned to generate the noise correlation map based on the pre-denoise CT image or the pre-denoise sinogram in the storage apparatus 139, input the pre-denoise CT image or the pre-denoise sinogram to the second learned model, and generate the noise correlation map by using the second learned model.

From the above, since the transmission amount of X-rays decreases at a thick portion of the subject P, even in the case where the noise relative to the detection signal of the X-rays relatively increases and the noise increases in the central portion of the sinogram or the tomographic image, the present medical X-ray CT apparatus 1 can effectively reduce the noise of the tomographic image of the subject P by using the sinogram or the tomographic image as the processing target signal 101 and using the noise correlation map calculated from the length of X-rays passing through the subject P as the reference signal 102.

As modifications of the present embodiment and various modification examples, the technical ideas of the present medical image diagnostic apparatus can be realized by installing the noise reduction programs on a computer such as a workstation and loading them in the memory. Here, the noise reduction program causes a computer to input the noise correlation map and the medical image or the intermediate image to the learned model functioned to generate the denoise image, in which the noise of the medical image or the noise of the intermediate image is reduced, based on the medical image generated based on the data collected with respect to the subject or the intermediate image at the front stage for generating the medical image, and the noise correlation map correlated with noise included in the medical image or the intermediate image, and generate the denoise image, in which the noise of the medical image or the noise of the intermediate image is reduced, by using the learned model. The program that allows the computer to perform the method can also be stored and distributed in various portable storage media such as a magnetic disk, an optical disk, a semiconductor memory, and the like.

As modifications of the present embodiment and various modification examples, the technical ideas of the present medical image diagnostic apparatus can be applied to a nuclear medical diagnostic apparatus, an X-ray diagnostic apparatus, and the like. Here, as the noise correlation map, for example, a map (hereinafter referred to as a detection sensitivity map) that indicates sensitivity of each of the plurality of detecting elements in the nuclear medical diagnostic apparatus, the X-ray diagnostic apparatus, and the like is used. The detection sensitivity map is collected, for example, upon calibration of the plurality of detecting elements in each of these apparatuses. Furthermore, as modifications of the present embodiment and various modification examples, the technical ideas of the present medical image diagnostic apparatus can also be applied to an ultrasound diagnostic apparatus. Here, as the noise correlation map 102, for example, a map (hereinafter referred to as a piezoelectric conversion map) that reflects piezoelectric conversion characteristics of each of a plurality of piezoelectric elements in an ultrasonic probe is used. The piezoelectric conversion map is collected, for example, upon calibration of each of the plurality of piezoelectric elements in the ultrasound diagnostic apparatus.

According to the medical image diagnostic apparatus of the embodiment, the modification example, and the application example, etc. explained above, noise reduction accuracy can be improved. That is, according to the present embodiment, the modification example, and the application example, etc., in addition to the processing target signal 101 of such as the noise reduction target image, the reference signal 102 of such as a noise amount map indicating the spatial distribution of the noise amount is input to the CNN 105, thereby providing a medical image diagnostic apparatus that can improve the accuracy of noise reduction.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image diagnostic apparatus comprising processing circuitry that
inputs a noise correlation map and data corresponding to a medical image or data corresponding to an intermediate image to a learned model, wherein the noise correlation map is a noise image correlated with a spatial distribution of noise amount in the medical image, the learned model is functioned to generate denoise image data, in which noise of the medical image or noise of the intermediate image is reduced, based on the medical image generated based on data collected with respect to a subject or the intermediate image at a front stage for generating the medical image and the noise correlation map correlated with the noise included in the medical image or the intermediate image, and
generates a denoise image from the denoise image data, in which the noise of the medical image or the noise of the intermediate image is reduced,
wherein
the learned model is a neural network, and
the processing circuitry:
inputs the data corresponding to the medical image or the data corresponding to intermediate image to an input layer of the neural network, and
directly inputs the noise correlation map to an intermediate layer in the neural network.

2. The medical image diagnostic apparatus according to claim 1, wherein
the data is magnetic resonance data,
the medical image is a magnetic resonance image,
the intermediate image is a complex number image, and
the noise correlation map corresponds to a map generated by using at least one of a sensitivity map that indicates spatial sensitivity of an RF coil related to collecting the magnetic resonance data, a g map that indicates distribution of a g-factor calculated based on the magnetic resonance data, a static magnetic field inhomogeneity map showing inhomogeneity of a static magnetic field, a gradient magnetic field inhomogeneity map showing inhomogeneity of a gradient magnetic field, and a density map that corresponds to density of data in a k-space, or at least two among the sensitivity map, the g map, the static magnetic field inhomogeneity map, the gradient magnetic field inhomogeneity map, and the density map.

3. The medical image diagnostic apparatus according to claim 1, wherein
the data is projection data,
the medical image is an X-ray computed tomography imaging image,
the intermediate image is a sinogram based on the projection data, and
the noise correlation map is a transmission length map that indicates a transmission length of the subject along a ray of X-rays passing through the subject for each view in the medical image, or is a transmission length reconstruction image that is reconstructed by using the transmission length map.

4. The medical image diagnostic apparatus according to claim 1, wherein the processing circuitry
inputs the data corresponding to medical image or the data corresponding to intermediate image to a second learned model that is functioned to generate the noise correlation map based on the medical image or the intermediate image, and
generates the noise correlation map.

5. The medical image diagnostic apparatus according to claim 1, wherein the processing circuitry is configured to reduce the noise in the intermediate image with an intensity corresponding to an amount of noise in partial regions of the image.

6. The medical image diagnostic apparatus according to claim 1, wherein
the data is magnetic resonance data,
the medical image is a magnetic resonance image,
the intermediate image is a complex number image, and
the noise correlation map corresponds to a map generated by using a g map that indicates distribution of a g-factor calculated based on the magnetic resonance data.

7. The medical image diagnostic apparatus according to claim 1, wherein the intermediate layer comprises:
a first layer configured to receive convoluted data from the input layer; and
a second layer configured to receive the noise correlation map and output of the first layer.

* * * * *